Figure 1:
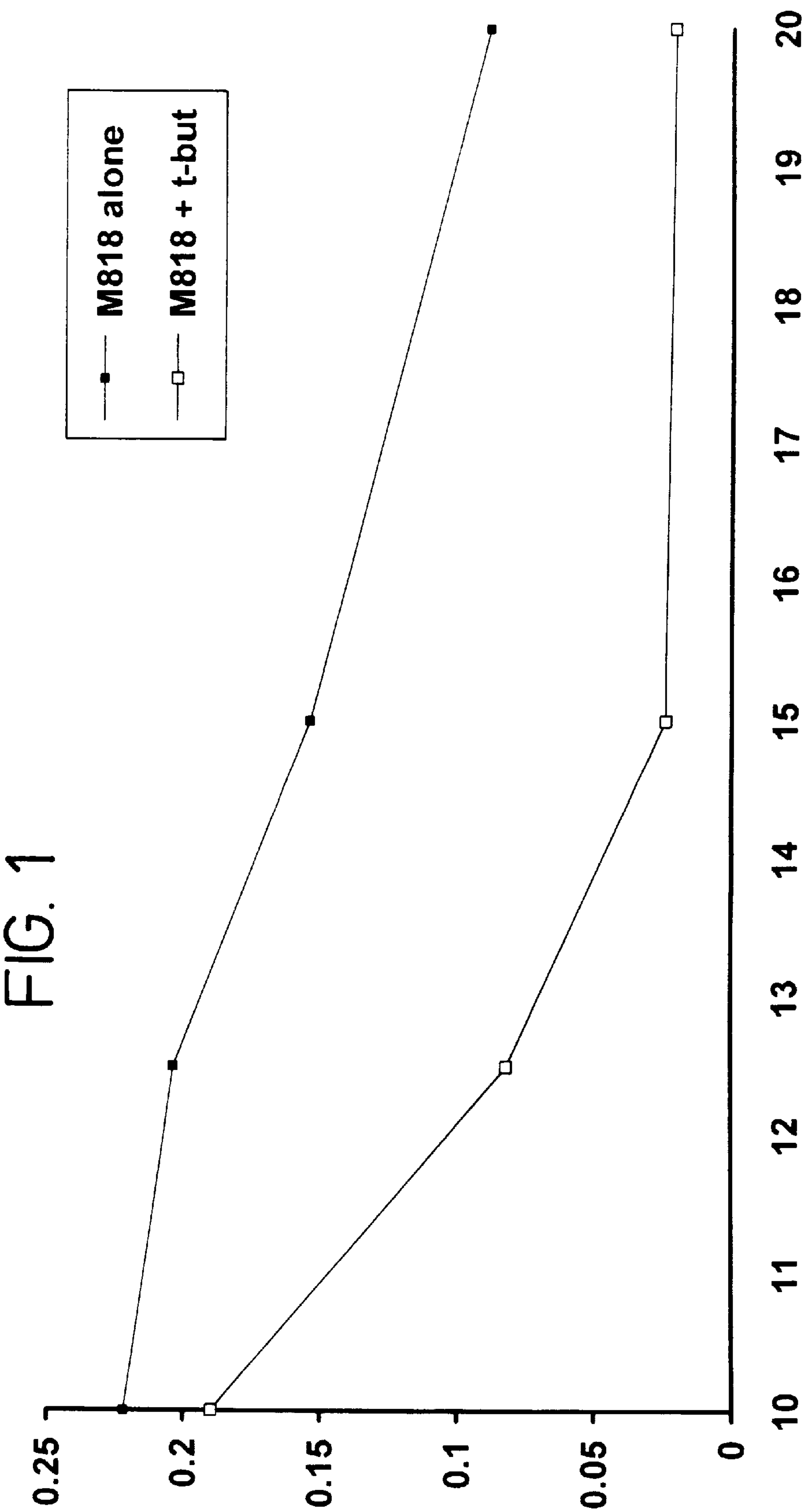

US005968549A

United States Patent [19]

New et al.

[11] Patent Number: 5,968,549

[45] Date of Patent: Oct. 19, 1999

[54] SOLUBILISATION AIDS

[75] Inventors: Roger Randal Charles New, London; Christopher John Kirby, Berkshire, both of United Kingdom

[73] Assignee: Cortecs (UK) Limited, United Kingdom

[21] Appl. No.: 08/870,516

[22] Filed: Jun. 6, 1997

Related U.S. Application Data

[63] Continuation of application No. PCT/GB95/02891, Dec. 8, 1995.

[30] Foreign Application Priority Data

Dec. 9, 1994 [GB] United Kingdom .................. 9424902

[51] Int. Cl.[6] .......................... A61K 9/127; B01J 13/02; B01J 13/04

[52] U.S. Cl. .......................................... 424/450; 264/4.1

[58] Field of Search ............................ 424/450; 264/4.1

[56] References Cited

FOREIGN PATENT DOCUMENTS

| | | |
|---|---|---|
| 0 366 277 A2 | 5/1990 | European Pat. Off. . |
| 0 521 994 B1 | 6/1997 | European Pat. Off. . |
| WO 91/14454 | 10/1991 | WIPO . |
| WO 95/13795 | 5/1995 | WIPO . |

OTHER PUBLICATIONS

Kirby et al, *Liposome Technology*, Volume, pp. 19–27. (1984) Gregoriadis, Ed., CRC Press, Inc., Boca Raton, Florida, USA.

U.S. Application No. 08/870,007, New et al., filed Jun. 6, 1997.

U.S. Application No. 08/870,435, Kirby, filed Jun. 6, 1997.

U.S. Application No. 08/856,514, New, filed May 15, 1997.

U.S. Application No. 08/648,065, New et al., filed May 15, 1996.

Kirby et al., *Bio/Technology*, 979–984 (Nov. 1984).

Okahata et al., J. Chem. Soc. Chem. Commun. 1392–1394 (1988).

*Primary Examiner*—Nathan M. Nutter
*Attorney, Agent, or Firm*—Pennie & Edmonds LLP

[57] ABSTRACT

The invention provides a process for the preparation of a single phase hyudrophobic preparation comprising a hydrophilic species in a hydrophobic solvent wherein a compound which is:

(a) a low molecular weight compound having at least some degree of polarity; and/or (b) a lipid-soluble organic acid; and/or (c) an amphiphile; and (d) glycerol or other polyhydric alcohols;

is added during the process to aid solubilisation.

14 Claims, 21 Drawing Sheets

SOLUBILISATION AIDS

This application is a continuation of PCT/GB95/02891 filed Dec. 8, 1995.

The present invention relates to the use of certain compounds as solubilisation aids for solubilising hydrophilic molecules in a hydrophobic phase in which they would not normally be soluble. In particular the present invention relates to the use of such solubilising aids for solubilising hydophilic macromolecules in a hydrophobic phase in which they would not normally be soluble.

For many applications, e.g in the pharmaceutical sciences, in food technology or the cosmetics industry, work with proteins and similar macromolecules presents problems because their hydrophilicity and high degree of polarity limit the extent to which they can interact with or incorporate into lipid phases. Many natural systems employ lipidic barriers (eg skin, cell membranes) to prevent access of hydrophilic molecules to internal compartments; the ability to disperse proteins in lipidic vehicles would open up a new route to introduction of these macromolecules into biological systems, whereby the lipid medium containing the protein can integrate with the hydrophobic constituents of barriers, instead of being excluded by them.

Dispersion of hydrophilic substances in oil phase rather than aqueous media confers other benefits in terms of increasing their stability with respect to temperature-mediated denaturation, hydrolysis, light sensitivity etc. Oils can be chosen which remain fluid over a wider temperature range than aqueous solutions, or that have a higher viscosity, resulting in greater protection against physical damage. In mixed-phase systems, sequestration of proteins in oil can limit mutually harmful interactions—eg oxidation—with water-soluble compounds.

There are examples of formulations containing both macromolecules and oil and one such example is disclosed in EP-A-0366277. The formulation disclosed in this document is an emulsion having both a hydrophobic and a hydrophilic phase, wherein the hydrophobic phase contains chylomicra or chylomicron-forming lipids. However, the macromolecule is dissolved in the hydrophilic phase not in the hydrophobic phase.

EP-A-0521994 also relates to a composition suitable for the oral delivery of macromolecules which comprises a biologically active material in association with lecithin or a compound capable of acting as a precursor for lecithin in vivo. All of the compositions exemplified are formulations which comprise a hydrophilic and a lipophilic phase. Once again, in this prior art document, the macromolecule is dissolved in the hydrophilic phase rather than in the lipophilic phase.

Although the formulations mentioned above do contain both macromolecules and oils, it is significant that in all cases the macromolecule is dissolved in the hydrophilic rather than in the lipophilic phase. Attempts to form true solutions of macromolecules in oils have met with limited success.

Okahata et al (*J. Chem. Soc. Chem. Commun.*, 1988, 1392–1394) disclose a process for solubilising proteins in a hydrophobic solvent. However, in the array of protein surrounded by amphiphile molecules produced by that method the authors stated that the amphiphile molecules reacted with the protein in the liquid medium by hydrogen bonding or via an electrostatic interaction to form a solid precipitate.

UK patent application No. 9323588.5 discloses a process by which a hydrophilic species can be solubilised in a hydrophobic solvent in which it would not normally be soluble. The process relies on the surprising discovery that if a hydrophilic species is mixed with an amphiphile under certain conditions, the resultant composition will be readily soluble in lipophilic solvents such as oils.

However, with some hydrophobic solvents, for example longer chain triglycerides, solubilisation is sometimes still difficult and there exists, therefore, a need for ways to increase the efficiency of solubilisation.

Surprisingly it has now been found that certain compounds can aid the solubilisation of the hydophilic species and hence facilitate the formation of a single phase hydrophobic preparation. This is particularly useful when the hydrophobic solvent includes medium or longer chain triglycerides.

Thus, in a first aspect the present invention provides a process for the preparation of a single phase hydrophobic preparation comprising a hydrophilic species, in a hydrophobic solvent, the process comprising:

(i) associating the hydrophilic species with an amphiphile in a liquid medium such that, in the liquid medium, there is no chemical interaction between the amphiphile and the hydrophilic species;

(ii) removing the liquid medium to leave an array of amphiphile molecules with their hydrophilic head groups orientated towards the hydrophilic species; and (iii) providing a hydrophobic solvent around the hydrophilic species/amphiphile array;

wherein a compound which is;

(a) a low molecular weight compound having at least some degree of polarity; and/or (b) a lipid-soluble organic acid; and/or (c) an amphiphile; and/or (d) glycerol or other polyhydric alcohols;

is added at one or more of the above-noted stages (i)–(iii).

In another aspect the present invention provides a process for the preparation of a single phase hydrophobic preparation comprising a hydrophilic species, in a hydrophobic solvent, the process comprising:

(i) associating the hydrophilic species with a phosphoryl choline containing amphiphile in a liquid medium such that, in the liquid medium, there is no chemical interaction between the amphiphile and the hydrophilic species;

(ii) removing the liquid medium to leave an array of amphiphile molecules with their hydrophilic head groups orientated towards the hydrophilic species; and (iii) providing a hydrophobic solvent around the hydrophilic species/amphiphile array;

wherein a compound which is;

(a) a low molecular weight compound having at least some degree of polarity; and/or (b) a lipid-soluble organic acid; and/or (c) a different amphiphile from that used above; and/or (d) glycerol or other polyhydric alcohols;

is added at one or more of the above-noted stages (i)–(iii).

Preferably, (a) described above for both aspects is a neutral lipid-soluble low molecular weight compound having at least some degree of polarity.

The use of such compounds as described herein make easier the formation of a single phase species in which a hydophilic species is solubilised in a hydrophobic solvent in which it would not normally be soluble. This is particularly advantageous when the hydrophobic solvent is one or more longer chain triglycerides. However, even in situations where the hydrophobic solvent is not a longer chain triglyceride the use of such compounds will ease formation of a single phase preparation, and may, for instance, reduce the time required to produce such single phase preparations.

Suitably, (a) can be a low molecular weight compound such as a carboxylic acid, an amino acid benzyl alcohol, ethanol, t-butanol, i-propanol, or glycerol mono-oleate;

(b) can be a carboxylic acid, phenol, p-cresol, phenylboronic acid, benzyl boric acid, phenyl-sulphonic acid, phenyl-arsenic acid, benzoic acid, salicylic acid, acetic acid, sorbic acid, valearic acid, oleic acid and caproic acid; and (c) can be selected from cholesterol hemisuccinate (Chems) , α-tocopherol, α-tocopherol succinate (αTS) phosphatidic acid (PA),phosphatidyl-glycerol, phosphatidyl-inositol and lyso derivatives of any of the phosphatides.

In the present invention the term “hydrophilic species” relates to any species which is generally soluble in aqueous solvents but insoluble in hydrophobic solvents.

In a preferred embodiment the solubilisation aid is added at stage (i) and/or is provided with the hydrophobic solvent at stage (iii).

The compounds are used at concentrations in the range of 0.1–75% of the total weight of preparation, preferably in the range 0.5–10%, and most preferably in the range 1–5%.

In the context of the present invention, the term “chemical interaction” relates to an interaction such as a covalent or ionic bond or a hydrogen bond. It is not intended to include van der Waals forces or other interactions of that order of magnitude.

Where the compound is added at stage (i) it is preferably selected from the group comprising amphiphiles or polyhydric alcohols.

A wide variety of macromolecules can suitably be solubilised according to the present invention. In general, the macromolecular compound will be hydrophilic or will at least have hydrophilic regions since there is usually little difficulty in solubilising a hydrophobic macromolecule in oily solutions. Examples of suitable macromolecules include proteins and glycoproteins, oligo and polynucleic acids, for example DNA and RNA, polysaccharides and supramolecular assemblies of any of these including, in some cases, whole cells, organelles or viruses (whole or parts thereof). It may also be convenient to co-solubilise a small molecule such as a vitamin in association with a macromolecule, particularly a polysaccharide such as a cyclodextrin. Small molecules such as vitamin B12 may also be chemically conjugated with macromolecules and may thus be included in the compositions.

Examples of particular proteins which may be successfully solubilised by the method of the present invention include insulin, calcitonin, haemoglobin, cytochrome C, horseradish peroxidase, aprotinin, mushroom tyrosinase, erythropoietin, somatotropin, growth hormone, growth hormone releasing factor, galanin, urokinase, Factor IX, tissue plasminogen activator, superoxide dismutase, catalase, peroxidase, ferritin, interferon, Factor VIII, melanin and fragments thereof (all of the above proteins can be from any suitable source). Other macromolecules which may be used are FITC-labelled dextran and RNA extract from Torulla yeast.

In addition to macromolecules, the process of the present invention is of use in solubilising smaller organic molecules. Examples of small organic molecules include glucose, ascorbic acid, carboxyfluorescin and many pharmaceutical agents, for example anti-cancer agents, but, of course, the process could equally be applied to other small organic molecules, for example other vitamins or pharmaceutically or biologically active agents. In addition molecules such as calcium chloride and sodium phosphate can also be solubilised using the process of the invention. Indeed, the present invention would be particularly advantageous for pharmaceutically and biologically active agents since the use of non aqueous solutions may enable the route by which the molecule enters the body to be varied, for example to increase bioavailability.

Another type of species which may be included in the hydrophobic compositions of the invention is an inorganic material such as a small inorganic molecule or a colloidal substance, for example a colloidal metal. The process of the present invention enables some of the properties of a colloidal metal such as colloidal gold, palladium, platinum or rhodium, to be retained even in hydrophobic solvents in which the particles would, under normal circumstances, aggregate. This could be particularly useful for catalysis of reactions carried out in organic solvents.

There are numerous amphiphiles which may be used in the present invention and zwitterionic amphiphiles such as phospholipids are among those which have been found to be especially suitable. Phospholipids having a phosphatidyl choline head group have been used with particular success and examples of such phospholipids include phosphatidyl choline (PC) itself, lyso-phosphatidyl choline (lyso-PC), sphingomyelin, derivatives of any of these, for example hexadecylphosphocholine or amphiphilic polymers containing phosphoryl choline and halogenated amphiphiles, e.g. fluoronated phospholipids. In the present application, the terms phosphatidyl choline (PC) and lecithin are used interchangeably. Suitable natural lecithins may be derived from any convenient source, for example egg and, in particular, soya. In most cases, it is preferable to select an amphiphile which is chemically similar to the chosen hydrophobic solvent and this is discussed in greater detail below.

The fact that the present inventors have found zwitterionic amphiphiles such as phospholipids to be particularly suitable for use in the process is a further indication of the significant differences between the present invention and the method of Okahata et al. Significantly, the authors of that prior art document concluded that anionic and zwitterionic lipids were completely unsuitable for use in their method and stated that they obtained zero yield of their complex using these lipids.

The hydrophobic solvent of choice will depend on the purpose for which the composition is intended, on the type of species to be solubilised and on the amphiphile. Suitable solvents include non-polar oils such as mineral oil, squalane and squalene, long chain fatty acids with unsaturated fatty acids such as oleic and linoleic acids being preferred, alcohols, particularly medium chain alcohols such as octanol and branched long chain alcohols such as phytol, isoprenoids, e.g. nerol and geraniol, terpineol, monoglycerides such as glycerol monooleate (GMO), other esters, e.g. ethyl acetate, amyl acetate and bornyl acetate, diglycerides and triglycerides, particularly medium chain triglycerides and mixtures thereof, halogenated analogues of any of the above including halogenated oils, e.g. long chain fluorocarbons or iodinated triglycerides, e.g. lipidiol.

Optimum results are generally obtained when the hydrophobic solvent and the amphiphile are appropriately matched. For example, with a solvent such as oleic acid, lyso-PC is a more suitable choice of amphiphile than PC, whereas the converse is true when the hydrophobic solvent is a triglyceride.

In addition, in some cases it has been found to be advantageous to add a quantity of the amphiphile to the hydrophobic solvent before it is brought into contact with the hydrophilic species/amphiphile array. This ensures that the amphiphile molecules are not stripped away from their positions around the hydrophilic species because of the high affinity of the amphiphile for the hydrophobic solvent.

It is very much preferred that the preparations of the invention are optically clear and this can be monitored by measuring turbidity at visible wave lengths and, in some cases, by checking for sedimentation over a period of time.

A hydrophile/amphiphile array in which the hydrophilic head groups of an amphiphile are orientated towards a hydrophilic species has been produced before but it has never been suggested that this type of composition may be soluble in lipophilic solvents.

Kirby et al, in *Bio/Technology*, November 1984, 979–984 and in *Liposome Technology*, Volume I, pages 19–27, Gregoriadis, Ed., CRC Press, Inc., Boca Raton, Fla., USA describe a method for the preparation of liposomes in which a phospholipid is suspended in distilled water to form small unilamellar vesicles or multilamellar vesicles, mixed with the material to be entrapped and freeze dried. The mixture is then rehydrated to give liposomes.

At the time of publication of this prior art there was extensive worldwide interest in the preparation of liposomes but the idea of producing a single phase hydrophobic preparation of a macromolecule seems either never to have been thought of or to have been dismissed as impossible or of little value. Certainly, there is no suggestion in any of the prior art that the intermediate arrays could be put to any other use than the preparation of liposomes. Even if a single phase hydrophobic preparation had been a desirable objective, the idea of adding a hydrophobic rather than a hydrophilic solvent would have been unlikely to have been taken seriously because there was a strong prejudice in the art against hydrophobic preparations of hydrophilic molecules.

The orientation of amphiphile molecules into an array with their hydrophilic head groups facing the moieties of a hydrophilic species can be achieved in several ways and examples of particularly suitable methods are discussed in more detail below.

In a first method, which has a similar starting point to the method described by Kirby et al, supra, a hydrophilic species is mixed with a dispersion of an amphiphile in a hydrophilic solvent, such that the amphiphile molecules form an assembly in which the hydrophilic head groups face outwards towards the hydrophilic phase which contains the hydrophilic species. The hydrophilic solvent is then removed to leave a dry composition in which the hydrophilic head groups of the amphiphile molecules are orientated towards the hydrophilic species.

In the method described by Okahata et al, a solution of a protein was also mixed with a dispersion of an amphiphile in water. However, significantly, the authors of that paper believed that it was necessary to obtain a precipitate which would then be soluble in hydrophobic solvents. Since many of the preferred amphiphiles of the present invention do not form such a precipitate, Okahata et al concluded that they would be of no use. In the process of the present invention, no precipitate is required and, indeed, it is generally thought to be undesirable to allow the formation of a precipitate since this results in a reduced yield of the required product.

In this first method, it is preferred that the hydrophilic solvent is water although other polar solvents may be used.

The form taken by the amphiphile assembly may be micelles, unilamellar vesicles, preferably small unilamellar vesicles which are generally understood to have a diameter of about 25 nm, multilamellar vesicles or tubular structures, for example cochleate cylinders, hexagonal phase, cubic phase or myelin type structures. The form adopted will depend upon the amphiphile which is used and, for example, amphiphiles such as phosphatidyl choline (PC) tend to form small unilamellar vesicles whereas lyso-phosphatidyl choline forms micelles. However, in all of these structures, the hydrophobic tails of the amphiphile molecules face inwards towards the centre of the structure while the hydrophilic head groups face outwards towards the solvent in which the hydrophilic species is dispersed.

The weight ratio of amphiphile:hydrophilic species will generally be in the region of from 1:1 to 100:1, preferably from 2:1 to 20:1 and most preferably about 8:1 for PC and 4:1 for lyso-PC.

These ratios are preferred ratios only and, in particular, it should be pointed out that the upper limit is set by economic considerations which mean that it is preferable to use the minimum possible amount of amphiphile. The lower limit is somewhat more critical and it is likely that ratios of 2:1 or below would only be used in cases where the hydrophilic species has a significant hydrophobic portion or is exceptionally large.

Good performance is obtained when the solvent is removed quickly and a convenient method for the removal of the solvent is lyophilisation, although other methods can be used.

In some cases, it may helpful to include salts in the hydrophilic solution, particularly if the hydrophilic species is a macromolecular compound such as a large protein. However, because the presence of larger amounts of inorganic salts tends to give rise to the formation of crystals and, hence, to a cloudy solution, it is preferred that organic salts are used rather than inorganic salts such as sodium chloride. Ammonium acetate is especially suitable for this purpose since it has the additional advantage that it is easily removed by freeze drying.

A second method for the preparation of a composition containing an array of amphiphiles with their head groups pointing towards the moieties of the hydrophilic species is to co-solubilise the hydrophilic species and the amphiphile in a common solvent followed by removal of the solvent.

The product of the process of the invention is new since it makes possible the production of single phase hydrophobic preparations comprising a hydrophilic species which would not normally be soluble in a hydrophobic solvent. Therefore, in a further aspect of the invention there is provided a single phase hydrophobic preparation comprising a hydrophilic species in a hydrophobic solvent obtainable by the process of the invention.

It may also be desirable to include other constituents in the single phase hydrophobic preparation in addition to the hydrophilic species. This is often particularly appropriate when the hydrophilic species is a macromolecule and, in that case, the preparation may include, for example, bile salts, vitamins or other small molecules which bind to or are otherwise associated with the macromolecules.

Although some macromolecule/amphiphile arrays were disclosed by Kirby et al, supra, the arrays disclosed were all intermediates in the formation of liposomes and, as discussed above, there has been no previous interest in non-liposomal or hydrophobic compositions comprising this type of entity. Therefore, the arrays of the present invention in which the amphiphile is one which does not form small unilamellar vesicles and would therefore not be expected to form liposomes are new.

One advantage of the preparations of the present invention is that they are essentially anhydrous and therefore stable to hydrolysis. They are also stable to freeze-thawing and have greater stability at high temperatures, probably because water must be present in order for the protein to unfold and become denatured. This means that they may be expected to have a much longer shelf life than aqueous preparations of the hydrophilic species.

The solutions of the present invention are extremely versatile and have many applications. They may either be used alone or they may be combined with an aqueous phase to form an emulsion or similar two phase composition which forms yet a further aspect of the invention.

In this aspect of the invention there is provided a two phase composition comprising a hydrophilic phase and a hydrophobic phase, the hydrophobic phase comprising a preparation of a hydrophilic species in a lipophilic solvent obtainable by a process as described herein.

Generally, in this type of composition, the hydrophobic phase will be dispersed in the hydrophilic phase.

The two phase compositions may be emulsions which may either be transient or stable, depending on the purpose for which they are required.

The average size of the emulsion particles will depend on the exact nature of both the hydrophobic and the aqueous phases. However, it may be in the region of 2 μm.

Dispersion of the hydrophobic preparation in the aqueous phase can be achieved by mixing, for example either by vigourous vortexing for a short time for example about 10 to 60 seconds, usually about 15 seconds, or by gentle mixing for several hours, for example using an orbital shaker.

Emulsions containing the hydrophobic preparations of the invention can also be used in the preparation of microcapsules. If the emulsion is formed from a gelatin-containing aqueous phase, the gelatin can be precipitated from the solution by coacervation by known methods and will form a film around the droplets of the hydrophile-containing hydrophobic phase. On removal of the hydrophilic phase, microcapsules will remain. This technology is known in the art, but has proved particularly useful in combination with the preparations of the present invention.

In other aspects the invention provides:

(i) the use of;
- (a) a low molecular weight compound having at least some degree of polarity; and/or
- (b) a lipid-soluble organic acid; and/or
- (c) an amphiphile; and/or
- (d) glycerol or other polyhydric alcohols;

in facilitating the solubilisation of a hydrophilic species in a hydrophobic solvent in which the hydrophilic species is not normally soluble;

(ii) a compound which is:
- (a) a low molecular weight compound having at least some degree of polarity; and/or
- (b) a lipid-soluble organic acid; and/or
- (c) an amphiphile; and/or
- (d) glycerol or other polyhydric alcohols;

for use in solubilising a hydrophilic molecule in a hydrophobic solvent in which it is not normally soluble; and (iii) the use of a compound which is;
- (a) a low molecular weight compound having at least some degree of polarity; and/or
- (b) a lipid-soluble organic acid; and/or
- (c) an amphiphile; and/or
- (d) glycerol or other polyhydric alcohols;

in the preparation of an agent for facilitating the solubilisation of a hydrophilic species in a hydrophobic solvent in which the hydrophilic species is not normally soluble.

One way in which the compositions of the present invention may be used is for the oral delivery to mammals, including man, of substances which would not, under normal circumstances, be soluble in lipophilic solvents. This may be of use for the delivery of dietary supplements such as vitamins or for the delivery of biologically active substances, particularly proteins or glycoproteins, including insulin and growth hormones.

In a further application, it is possible to encapsulate or microencapsulate, for example by the method described above, nutrients such as vitamins which can then be used, not only as human food supplements but also in agriculture and aquaculture, one example of the latter being in the production of a food stuff for the culture of larval shrimps.

In addition, the compositions find application in the preparation of pharmaceutical or other formulations for parenteral administration, as well as for use in topical or opthalmic applications. For this application, it is often preferable to use an emulsion of the oil solution and an aqueous phase as described above.

Many therapeutic and prophylactic treatments are intended for sustained or delayed release or involve a two component system, for example including a component for immediate release together with a component for delayed or sustained release. Because of their high stability, the preparations of the invention are particularly useful for the formulation of a macromolecule intended for sustained or delayed release.

The longer shelf life of the compositions of the present invention is a particular advantage in the pharmaceutical area.

The hydrophile-in-oil preparations may find application in the pharmaceutical or similar industries for flavour masking. This is a particular problem in the pharmaceutical industry since many drugs have unpleasant flavours and are thus unpopular with patients, especially children.

A further use is in the cosmetics industry where, again, hydrophobic preparations of hydrophilic compounds can very easily be incorporated into a cosmetic formulation. Examples of macromolecules which may be used in this way include those with antioxidant, moisturising or enzymatic action of some sort. The invention can also be used for the incorporation of proteins such as collagen into dermatological creams and lotions.

Finally, the invention has numerous uses in the field of chemical and biological synthesis, for example, non-aqueous enzymatic synthesis.

Figure 2:
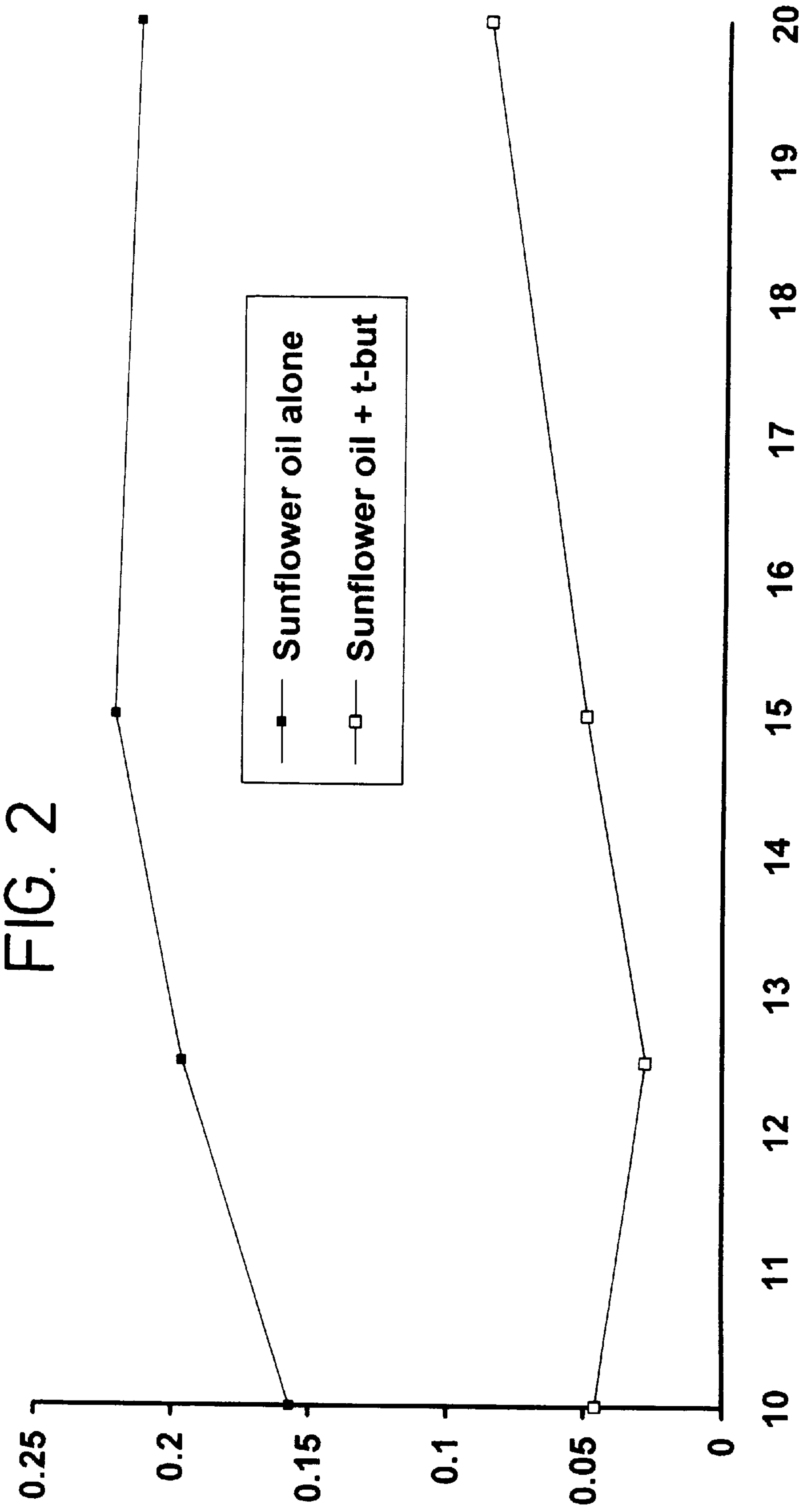
Figure 3:
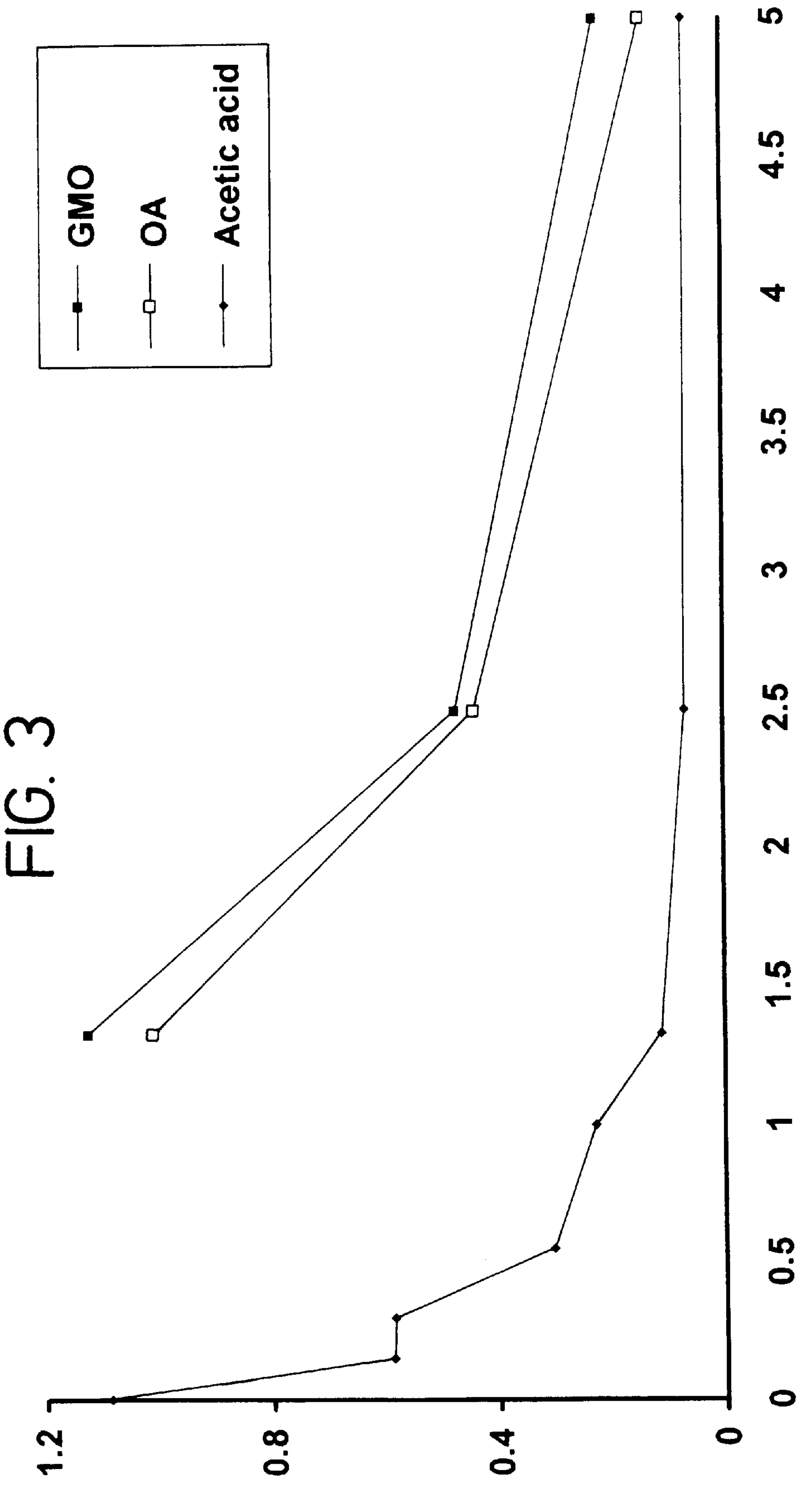
Figure 4:
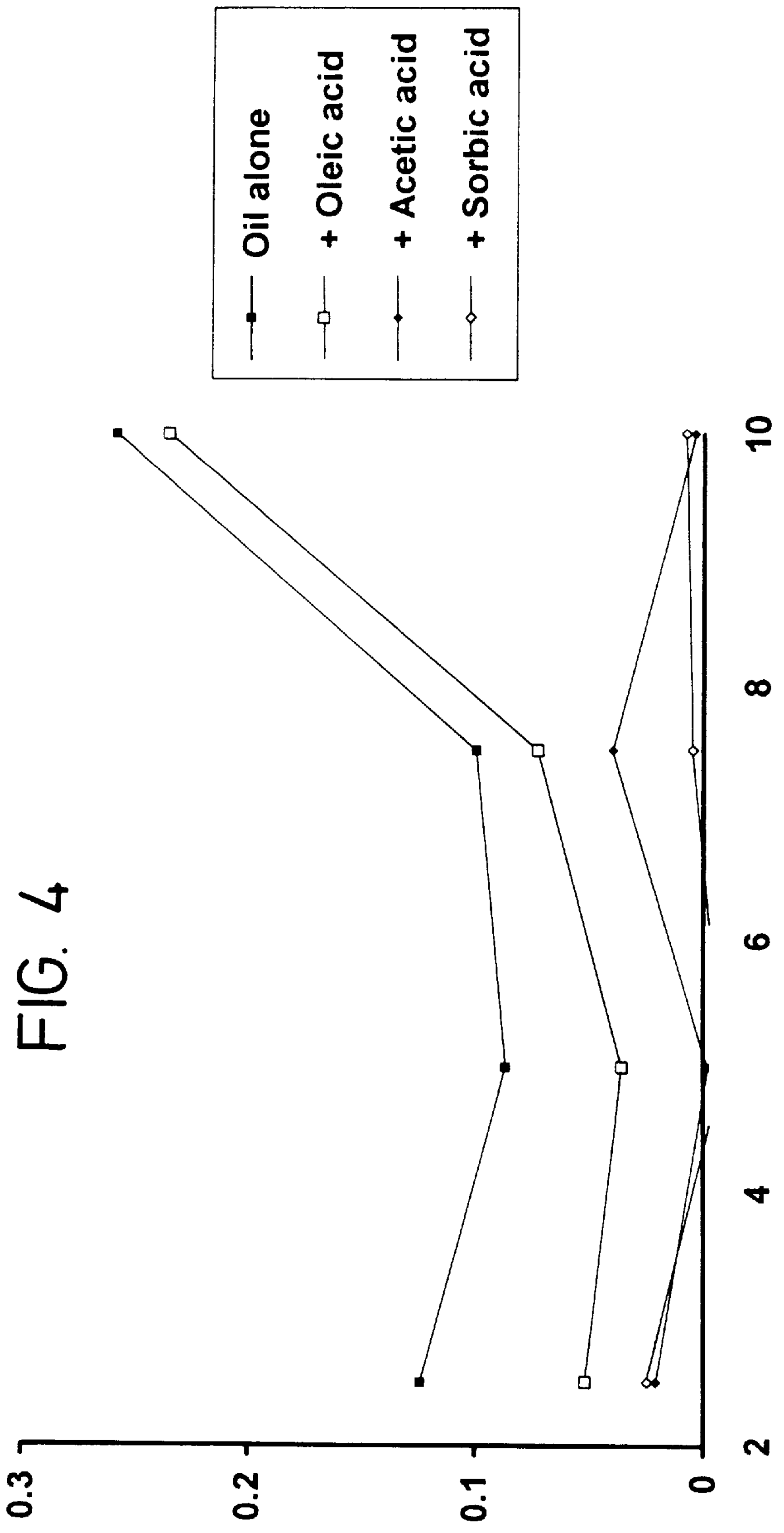
Figure 5:
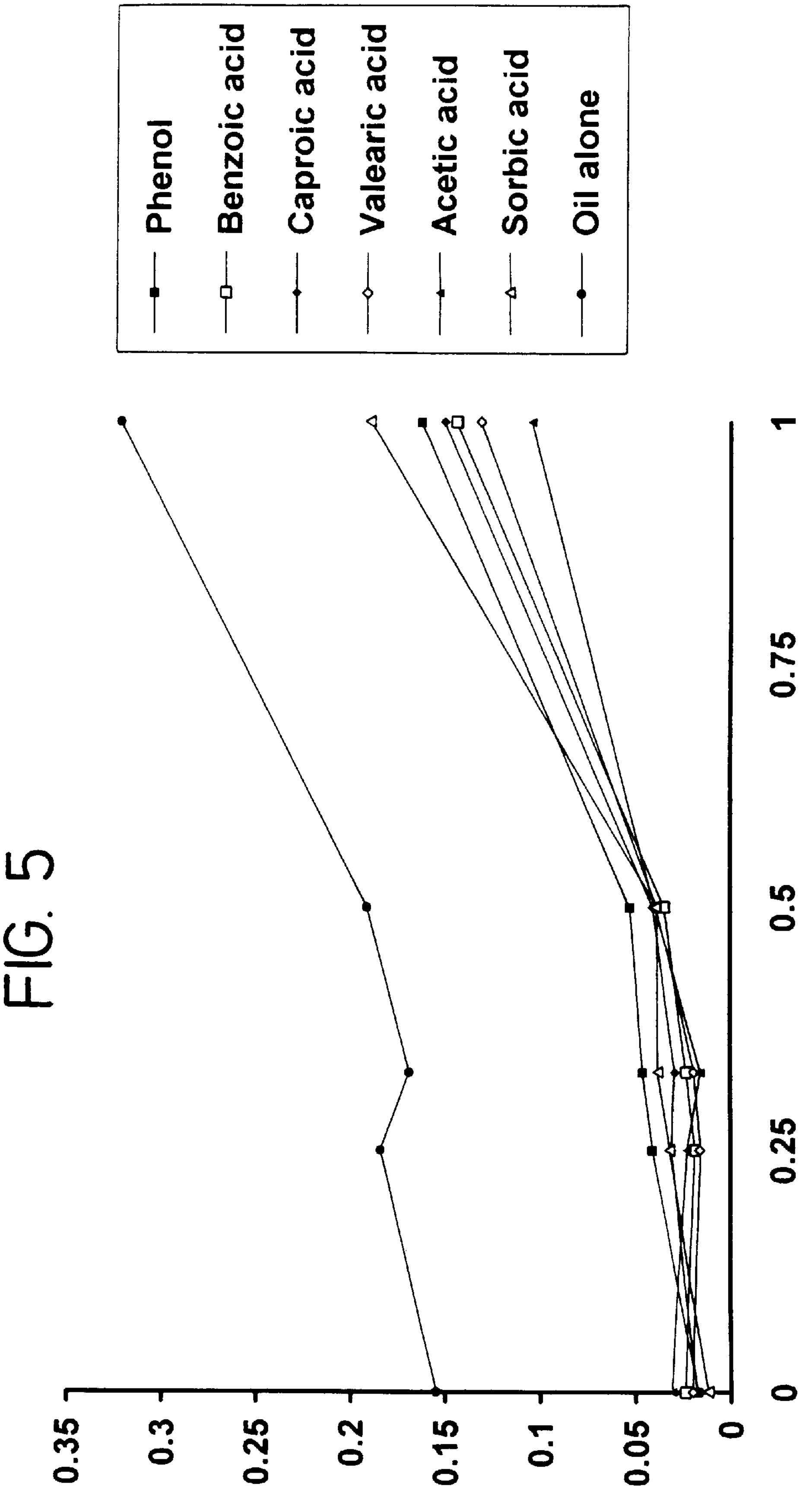
Figure 6:
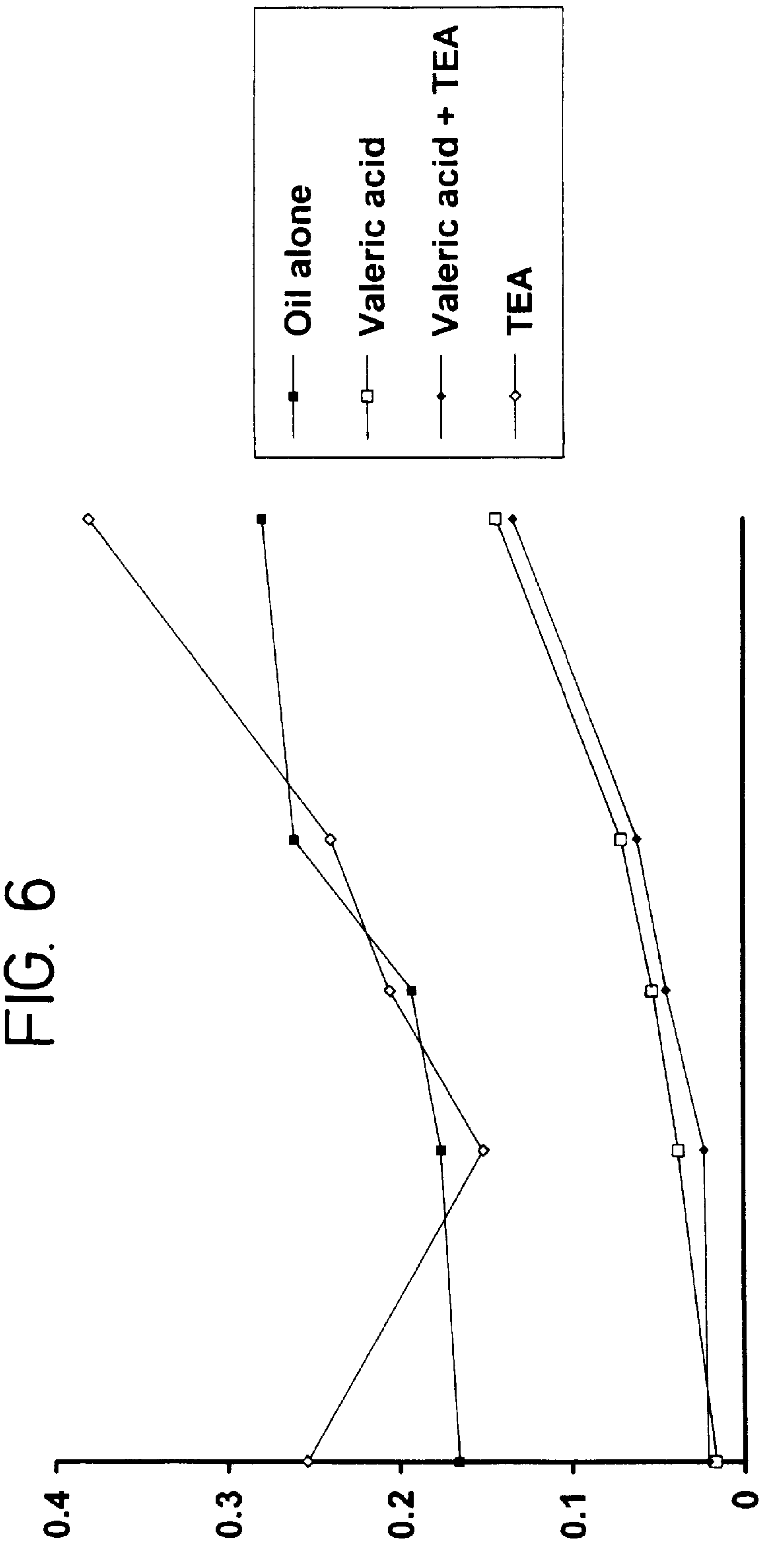
Figure 7:
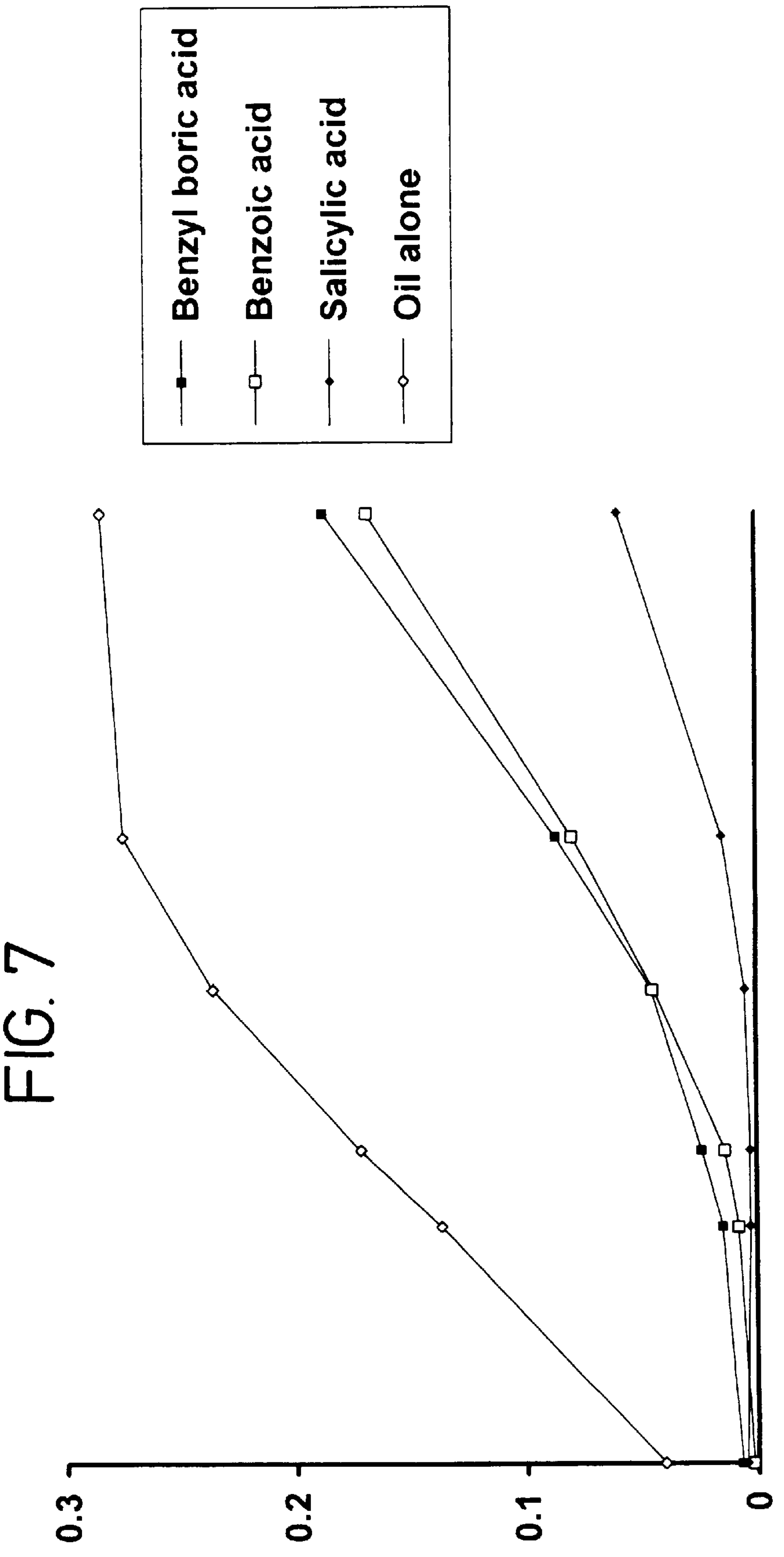
Figure 8:
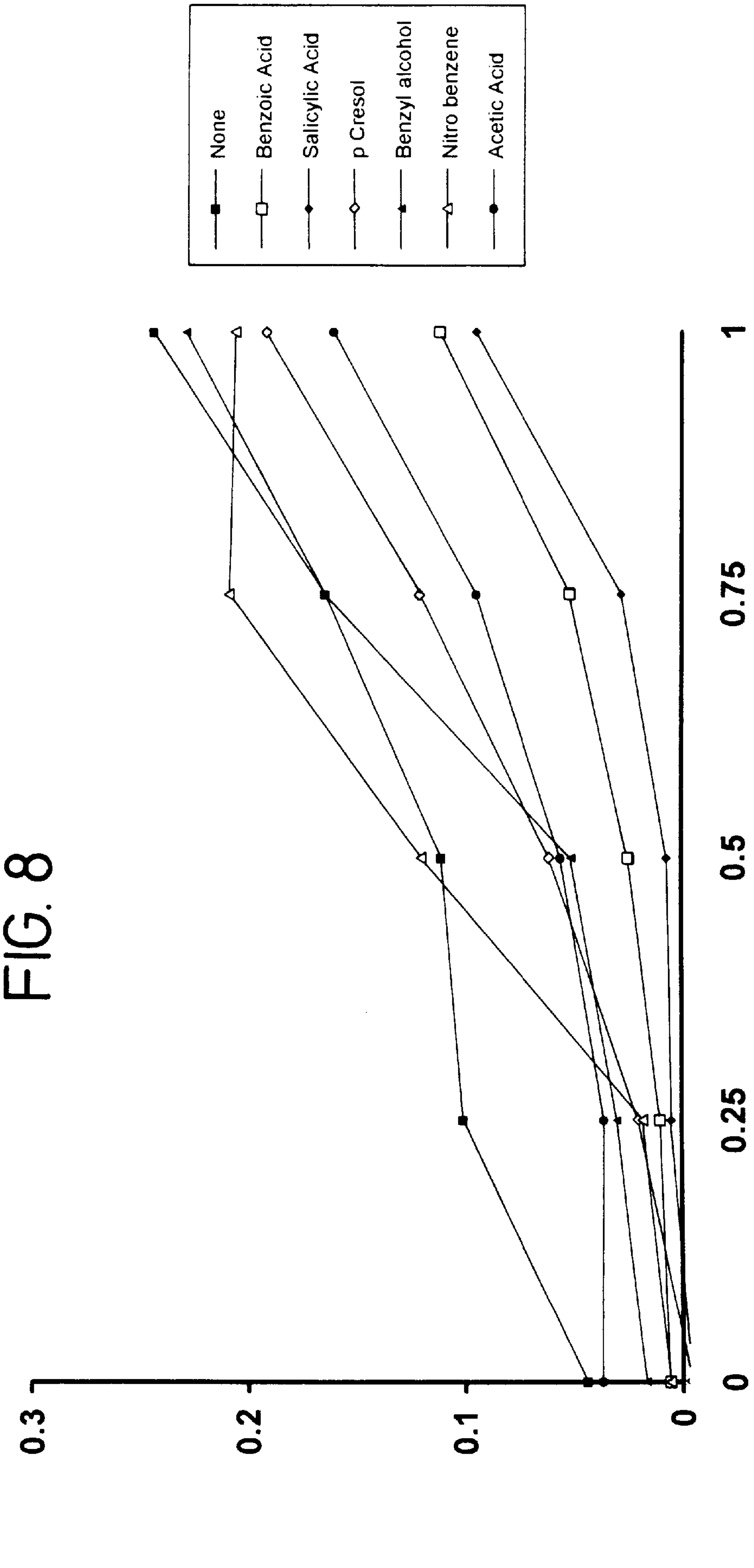
Figure 9:
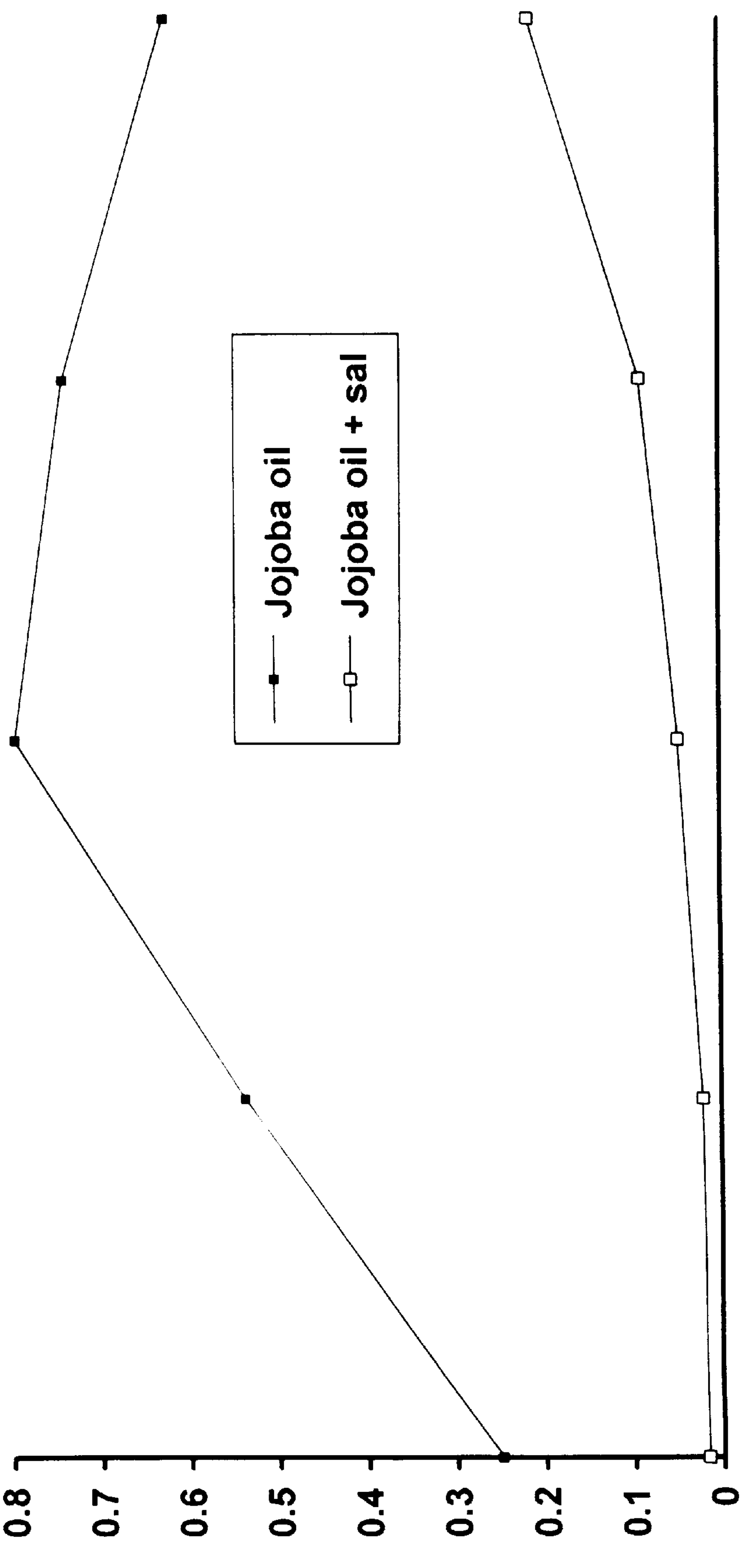
Figure 10:
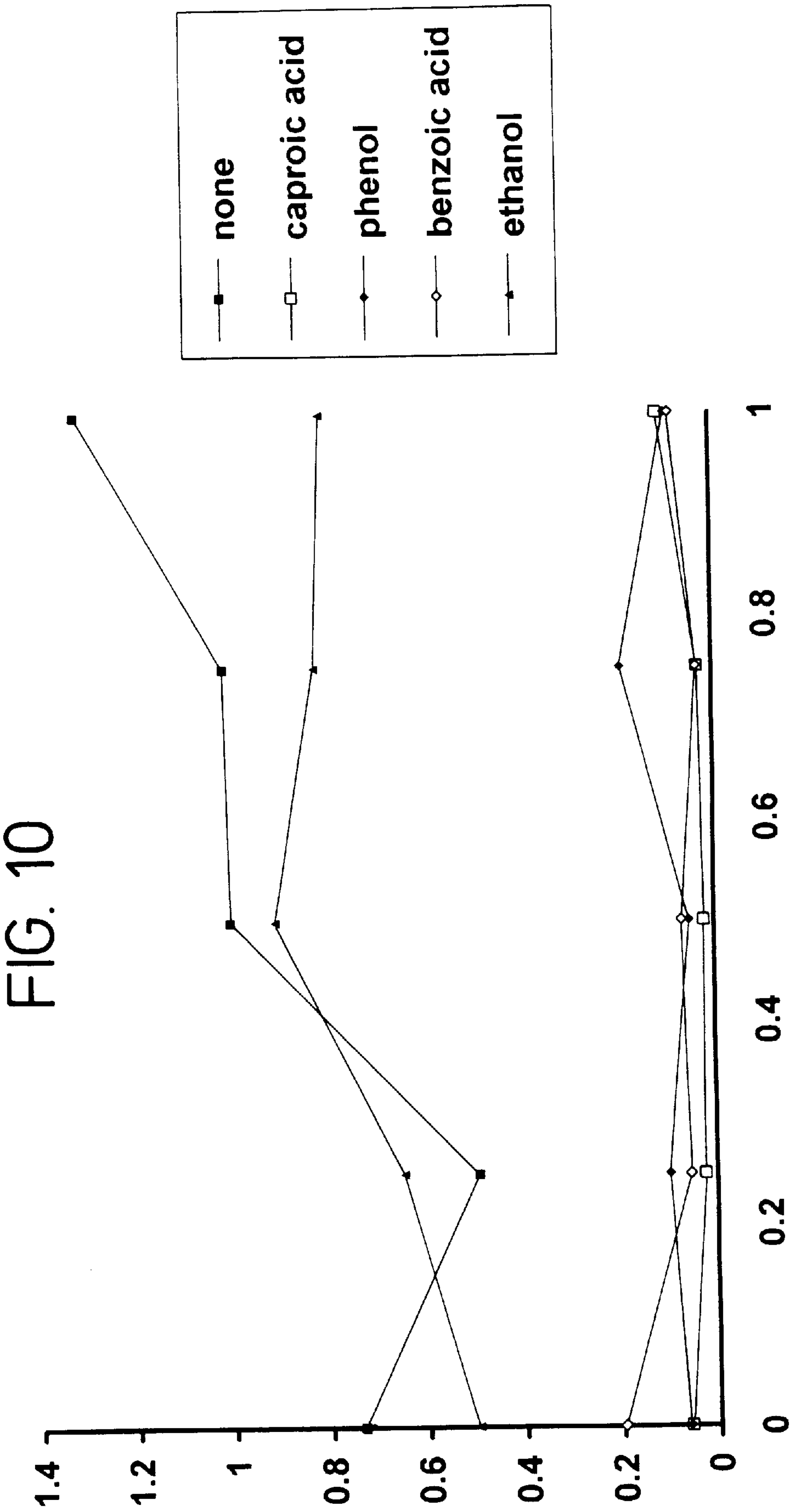
Figure 11:
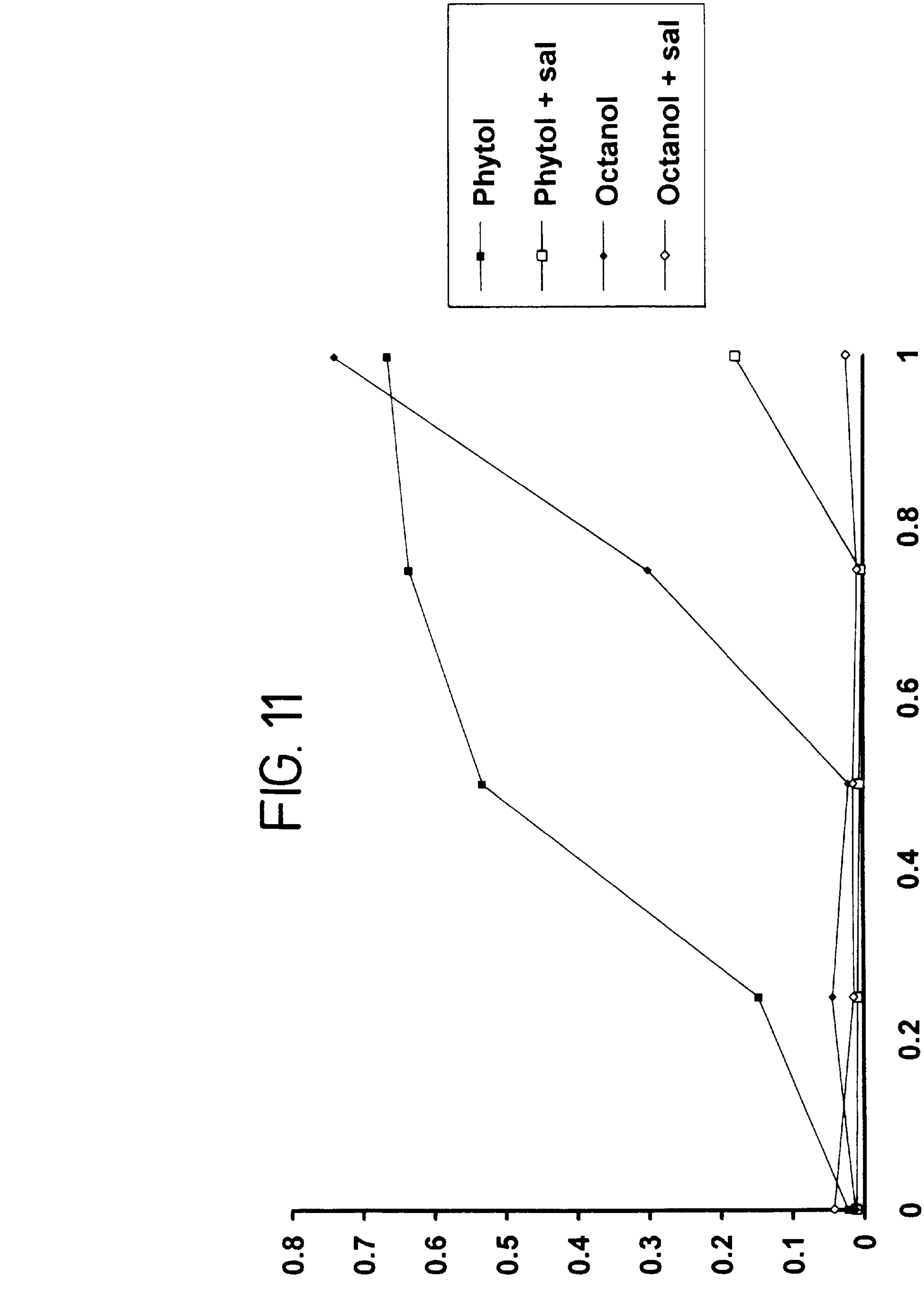
Figure 12:
Figure 13:
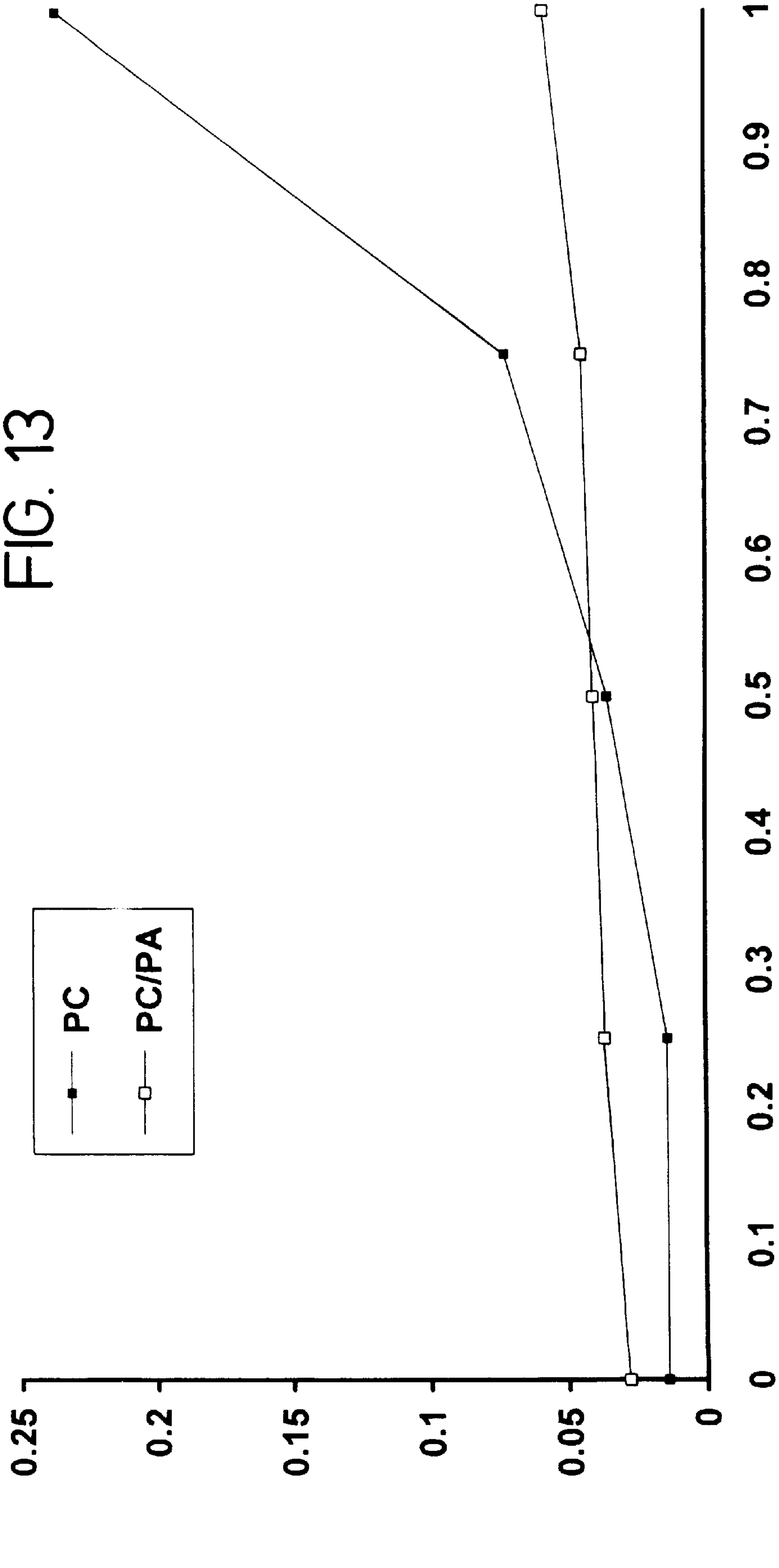
Figure 14:
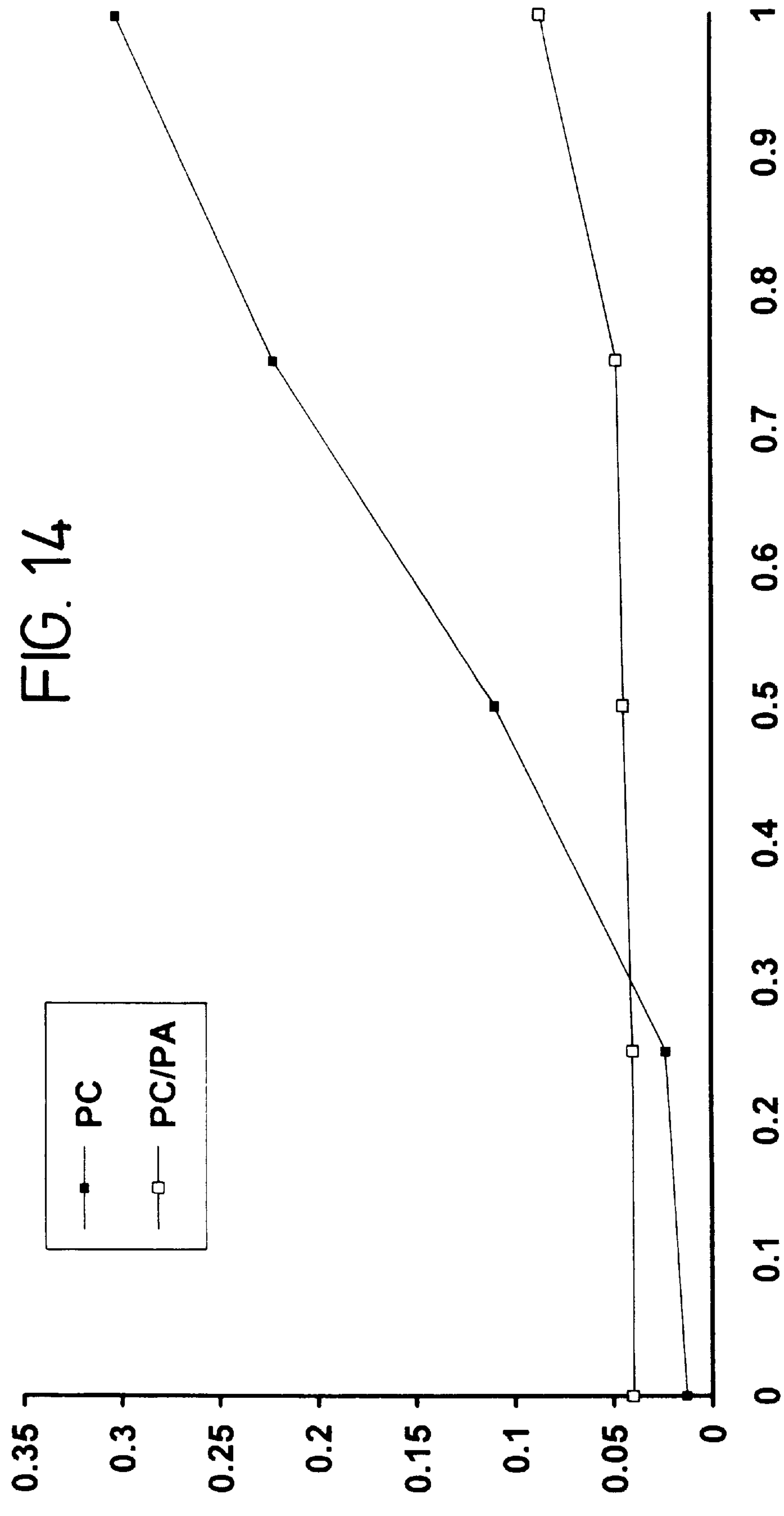
Figure 15:
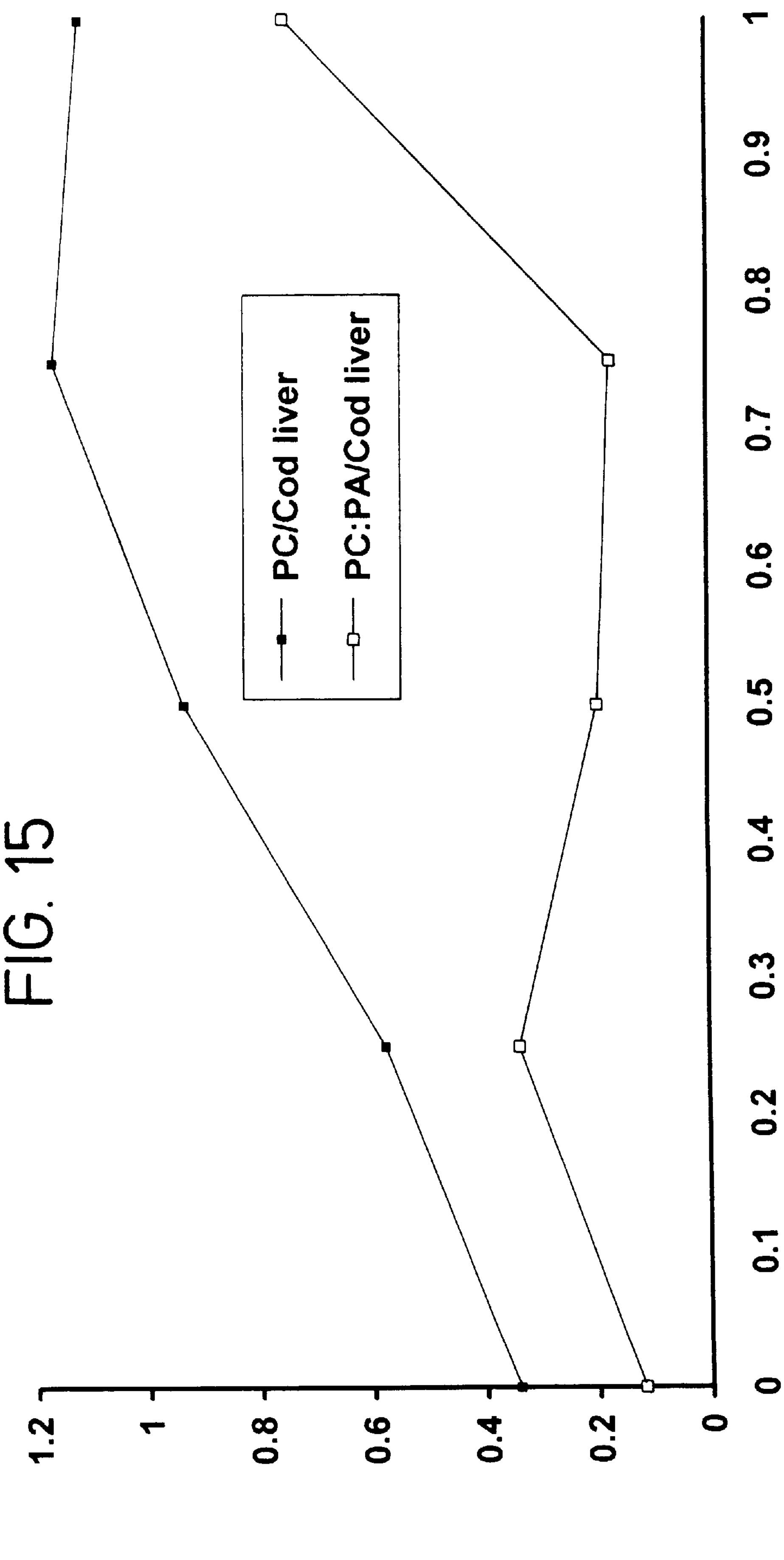
Figure 16:
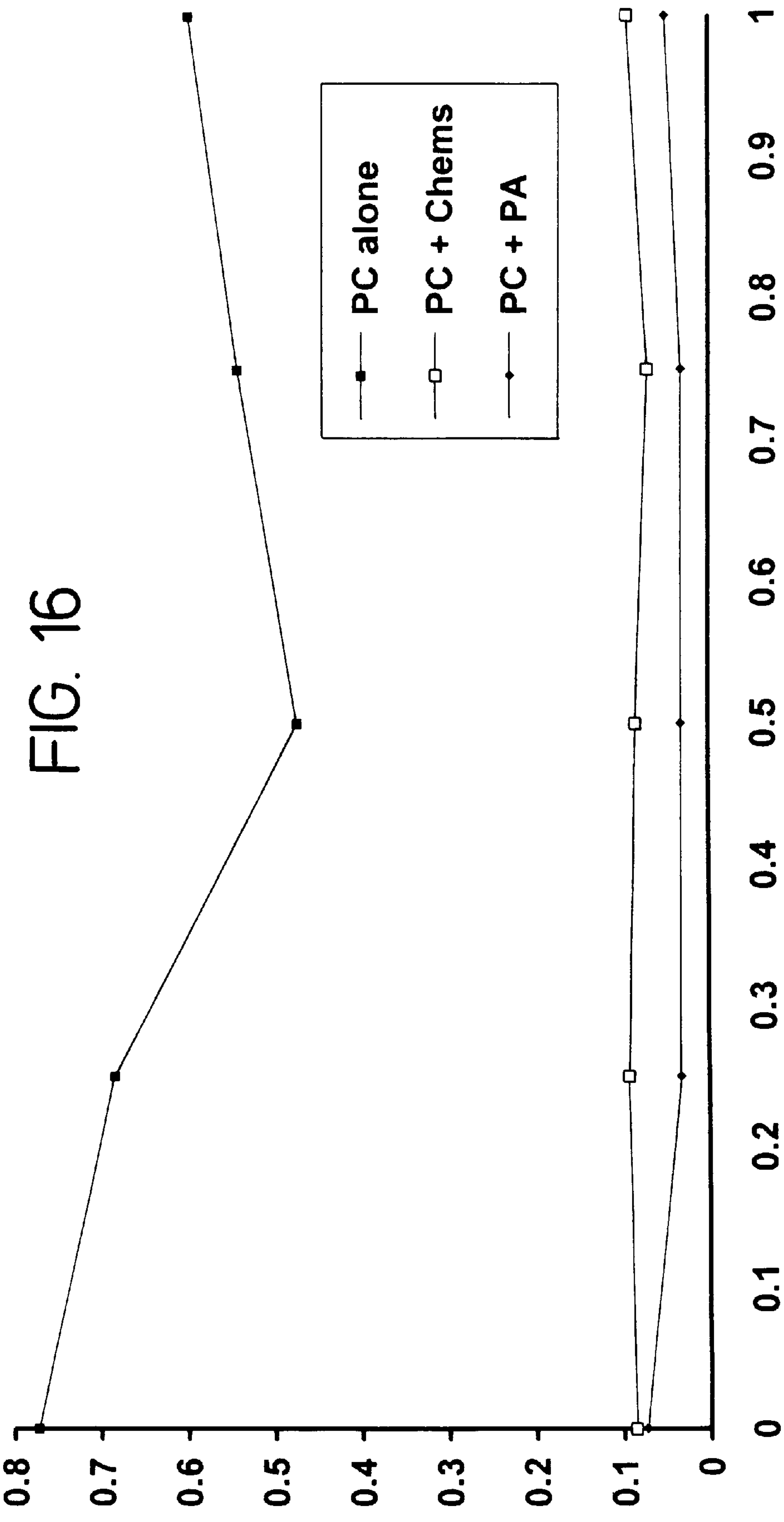
Figure 17:
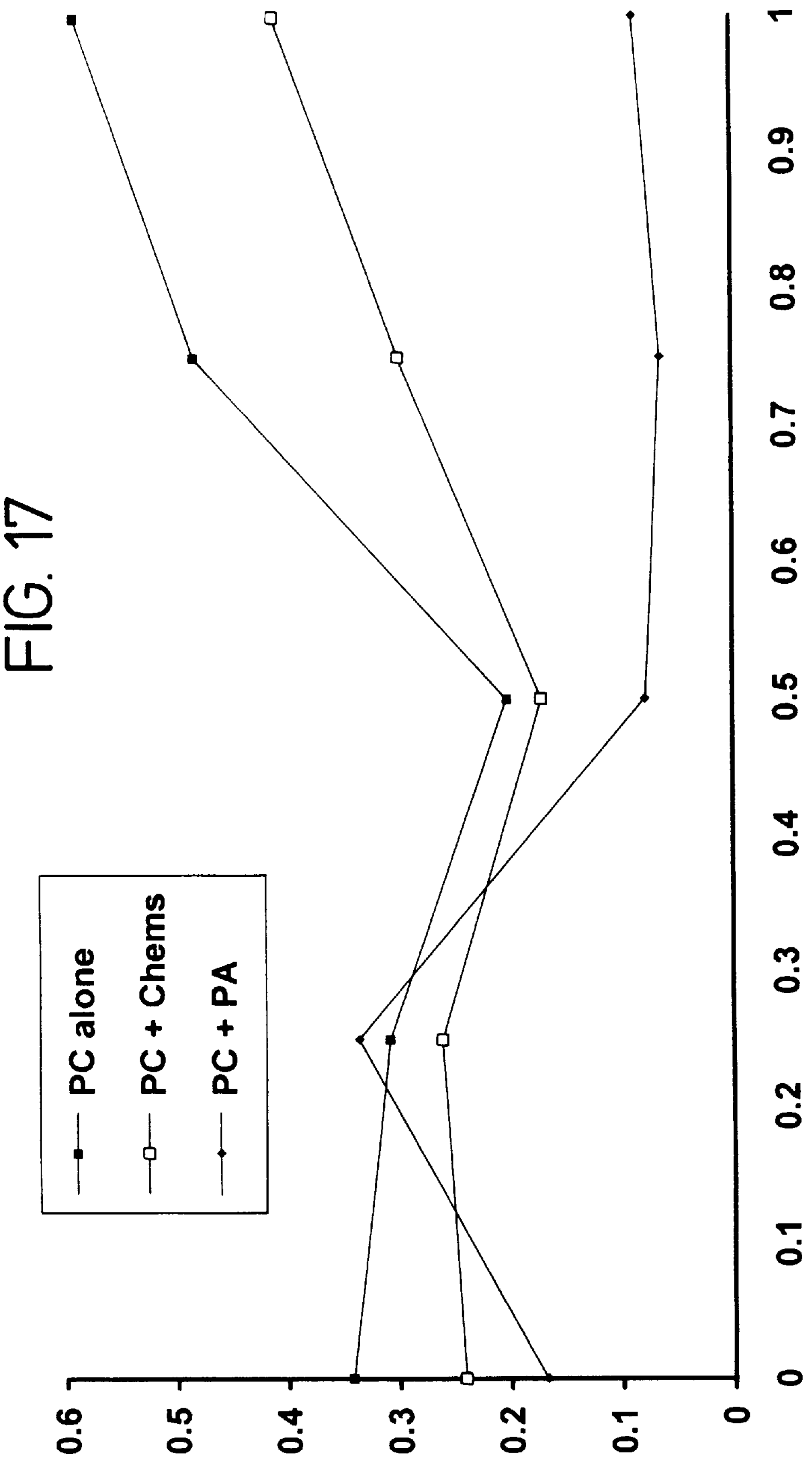
Figure 18:
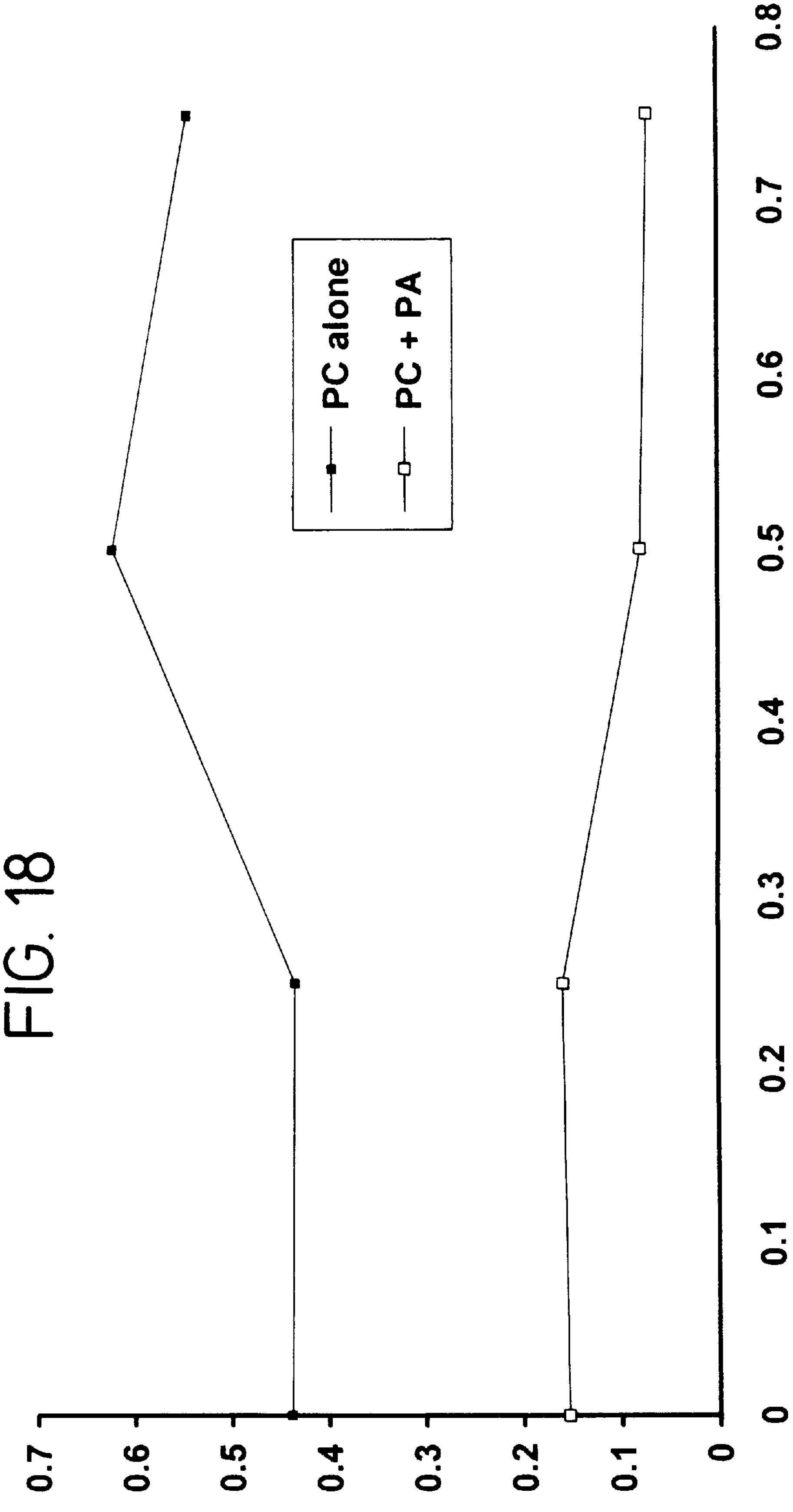
Figure 19:
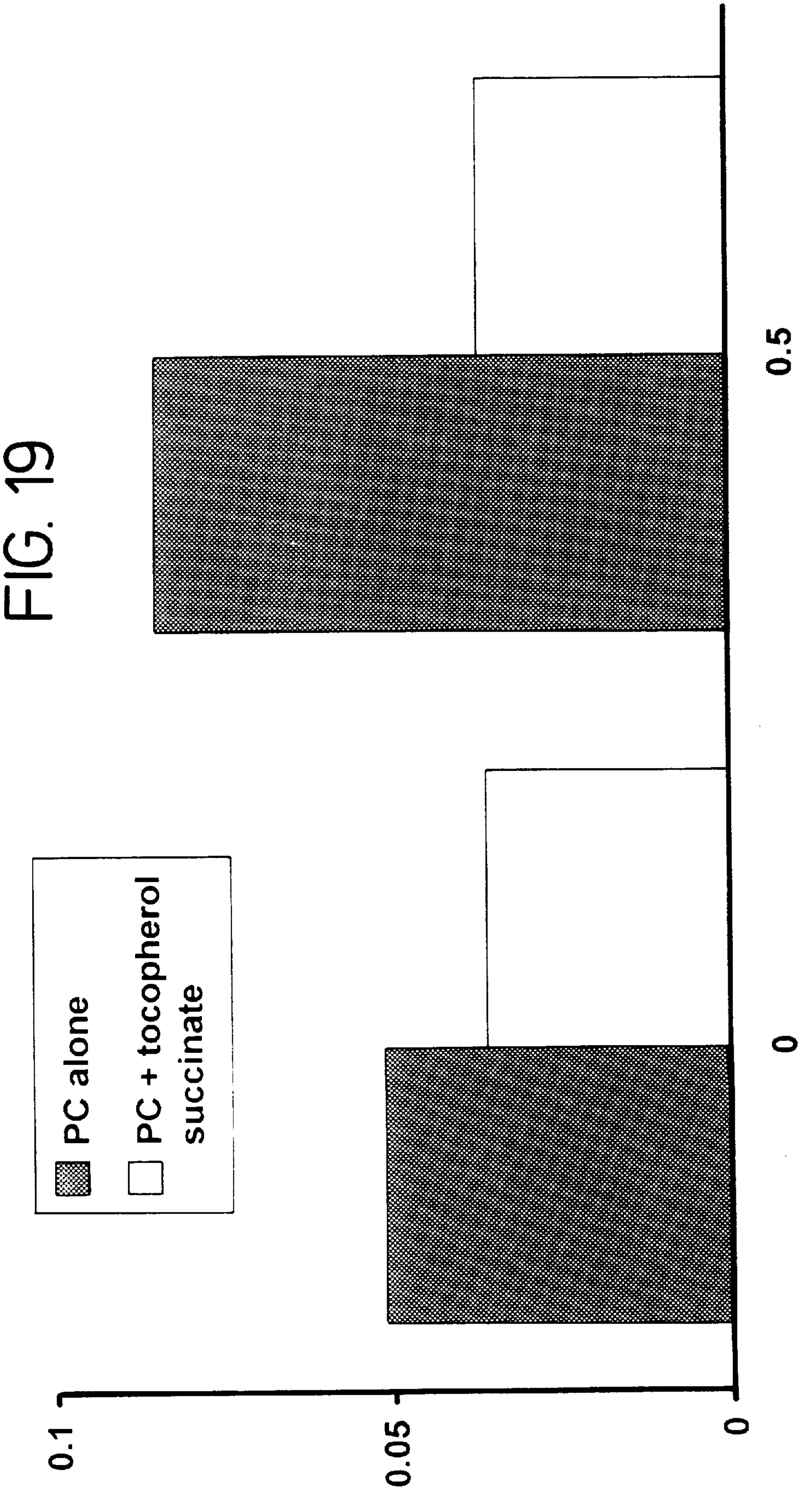

The invention will now be described with reference to the following examples. The examples refer to the figures in which:

FIG. 1: shows the effect of t-butanol in facilitating solubilisation of aprotinin in Miglyol 818;

FIG. 2: shows the effect of t-butanol in facilitating solubilisation of aprotinin in Sunflower oil;

FIG. 3: shows the effect of GMO, OA or Acetic acid on solubilisation of aprotinin in Sunflower oil;

FIG. 4: shows the effect of Acetic acid, sorbic acid and OA on the solubilisation of aprotinin in Sunflower oil;

FIG. 5: shows the effect of phenol, benzoic acid, caproic acid, valearic acid, acetic acid and sorbic acid on the solubilisation of aprotinin in Sunflower oil;

FIG. 6: shows the effect of valearic acid and triethylamine, alone or in combination, on the solubilisation of aprotinin in Sunflower oil;

FIG. 7: shows the effect of benzyl boronic acid, benzoic acid and salicylic acid on the solubilisation of aprotinin in Sunflower oil;

FIG. 8: shows the effect of benzoic acid, salicylic acid, p-cresol, benzoyl alcohol, nitrobenzene and acetic acid on the solubilisation of aprotinin in Sunflower oil;

FIG. 9: shows the effect salicylic acid on the solubilisation of aprotinin in jojoba oil;

FIG. 10: shows the effect of caproic acid, phenol, benzoic acid and ethanol on the solubilisation of aprotinin in squalane;

FIG. 11: shows the effect of salicylic acid on the solubilisation of aprotinin in either phytol or octanol;

FIG. 12: shows the effect of different concentrations of sorbic acid on the solubilisation of aprotinin in Sunflower oil;

FIG. 13: shows the effect of phosphatidic acid on the solubilisation of aprotinin in Miglyol 818;

FIG. 14: shows the effect of phosphatidic acid on the solubilisation of aprotinin in oleic acid;

FIG. 15: shows the effect of phosphatidic acid on the solubilisation of aprotinin in cod liver oil;

FIG. 16: shows the effect of either phosphatidic acid or cholesterol hemisuccinate on the solubilisation of aprotinin in Squalane;

FIG. 17: shows the effect of either phosphatidic acid or cholesterol hemisuccinate on the solubilisation of aprotinin in Sunflower oil;

FIG. 18: shows the effect of phosphatidic acid on the solubilisation of aprotinin in jojoba oil; and FIG. 19: shows the effect of α-tocopherol on the solubilisation of aprotinin in Miglyol 818.

Figure 20:
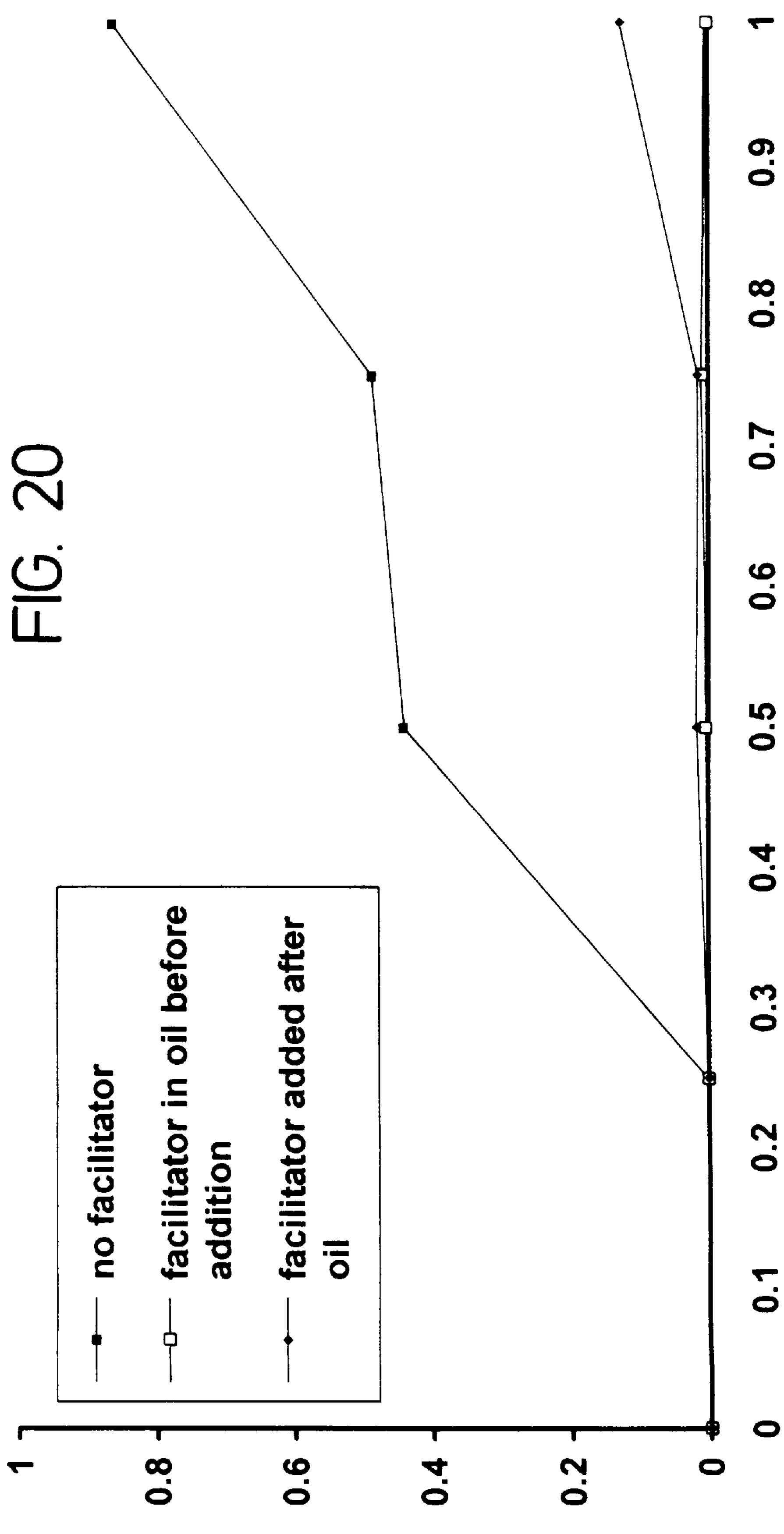

FIG. 20: shows the effect of salicylic acid, added before or after the oil, on the solubilisation of aprotinin in Miglyol 818.

Figure 21:
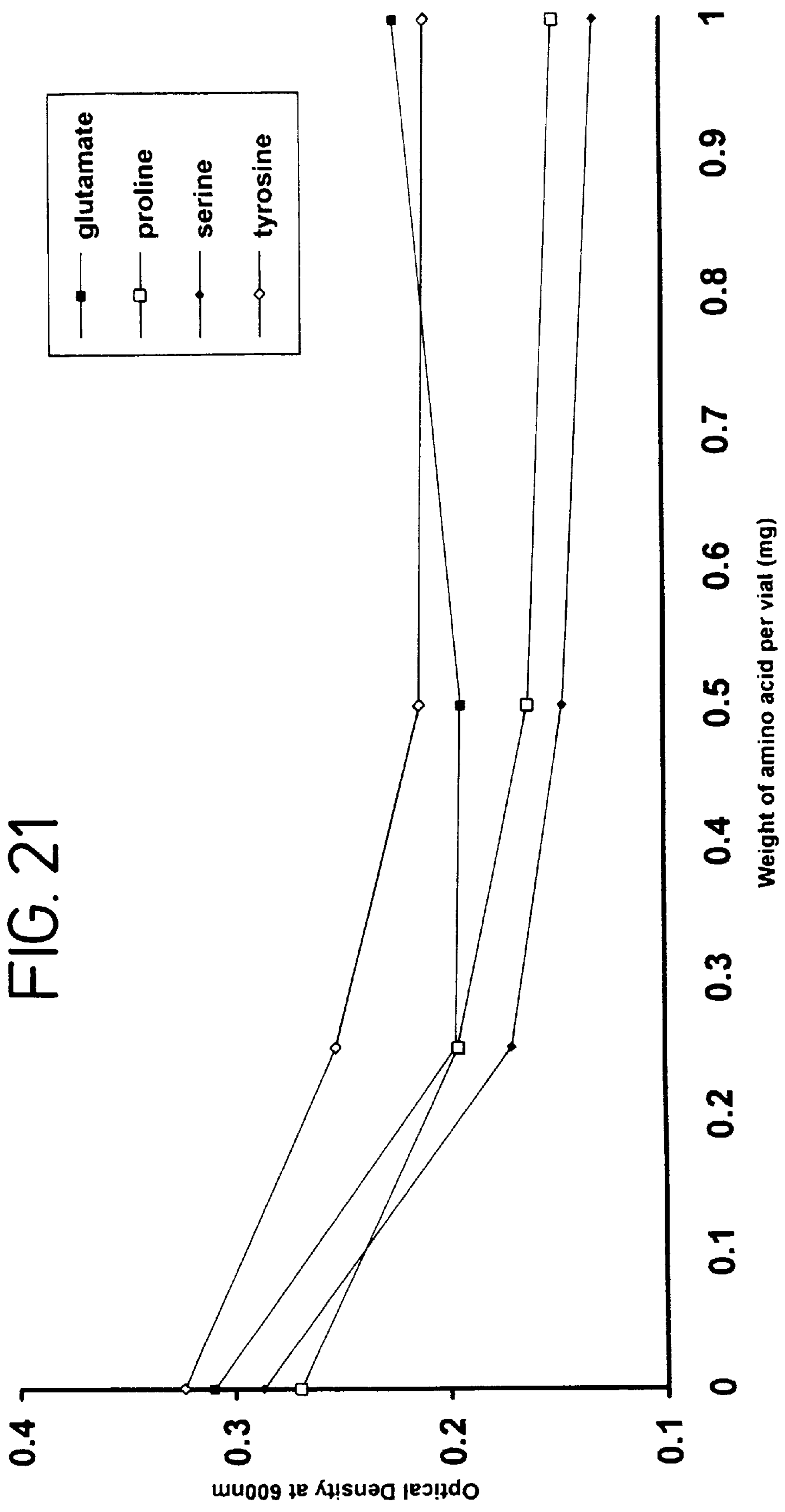

FIG. 21: shows the effect of the addition of amino acids to the aqueous phase during incorporation of ovalbumin into Miglyol M840.

EXAMPLE 1

Aprotinin was dissolved in distilled water at a concentration of 20 mg/ml and dispensed into wells of a microplate, each well receiving 50 μl. In addition, all wells received soya phosphatidyl choline, dispersed in distilled water by probe sonication for ten minutes with cooling, at a concentration of 100 mg/ml, each well in a row of four receiving 100, 125, 150 and 200 μl respectively. The contents of the wells were mixed by gentle shaking, then frozen at −20° C., then lyophilised overnight.

The following day, various oils, with or without additives, were added to the wells in each row. The plate was shaken gently for several hours, and optical density measurements were taken at intervals with a plate-reader at 550 nm. A low absorbance value indicates a low level of scattering, and corresponds to effective dispersion of protein in oil.

Employing the method described above, the effect of addition of tertiary butanol to Miglyol 818 or sunflower oil in facilitating dispersion of aprotinin, using soya phosphatidyl choline as amphiphile, is demonstrated. The results, expressed in terms of optical density as a function of phosphatidyl choline concentration after removal of tertiary butanol by lyophilisation (at constant protein concentration) are given in the table and are shown in FIGS. 1 and 2.

Initially, dispersions were performed by adding 100 μl of the pure oil, or 200 μl of a 50:50 vol:vol mixture of oil and t-butanol. After measurement of optical density, the samples were then frozen and the t-butanol was removed by lyophilisation. The OD of the resultant oils was measured again. Subsequent experiments have demonstrated that residual t-butanol in triglycerides after lyophilisation in no greater than 7% wt:wt.

| | mg of PC per well | | | |
|---|---|---|---|---|
| OD @ 550 nm | 10 | 12.5 | 15 | 20 |
| M818 alone | 0.222 | 0.204 | 0.154 | 0.089 |
| M818 + t-but | 0.19 | 0.082 | 0.024 | 0.021 |
| Sunflower oil alone | 0.157 | 0.197 | 0.222 | 0.215 |
| Sunflower oil + t-but | 0.046 | 0.028 | 0.05 | 0.087 |

EXAMPLE 2

Aprotinin was dissolved in distilled water at a concentration of 10 mg/ml and dispensed into wells of a microplate, each well receiving 100 μl. In addition, all wells received soya phosphatidyl choline, dispersed in distilled water by probe sonication for ten minutes with cooling, at a concentration of 100 mg/ml, each well in a row of eight receiving 125 μl. The contents of the wells were mixed by gentle shaking, then frozen at −20° C., then lyophilised overnight.

The following day, sunflower oil, with varying percentages of additives, was added to the wells in each row. The plate was shaken gently for eighteen hours, and optical density measurements were taken with a plate-reader at 550 nm. A low absorbance value indicates a low level of scattering, and corresponds to effective dispersion of protein in oil.

Employing the method described above, the effect of addition of glycerol mono-oleate, oleic acid and acetic acid to sunflower oil in facilitating dispersion of aprotinin, using soya phosphatidyl choline as amphiphile, is demonstrated. The results, expressed in terms of optical density as a function of concentration of additive (at constant protein and phosphatidyl choline concentration) are given in the table and FIG. 3.

| Additives | % Additives wt:wt | | | | | | | |
|---|---|---|---|---|---|---|---|---|
| employed | 0 | 0.15 | 0.3 | 0.55 | 1 | 1.33 | 2.5 | 5 |
| GMO | | | | | | 1.129 | 0.477 | 0.226 |
| OA | | | | | | 1.013 | 0.444 | 0.144 |
| Acetic Acid | 1.088 | 0.588 | 0.586 | 0.304 | 0.229 | 0.113 | 0.069 | 0.068 |

EXAMPLE 3

Aprotinin was dissolved in distilled water at a concentration of 20 mg/ml and dispensed into wells of a microplate, each well in a row of five receiving 12.5 μl. In addition, soya phosphatidyl choline, dispersed in distilled water by probe sonication for ten minutes with cooling, was added to each well at a concentration of 100 mg/ml, wells in each row receiving 0, 25, 50, 75 and 100 μl respectively. The contents of the wells were mixed by gentle shaking, then frozen at −20° C., then lyophilised overnight.

The following day, 100 μl of sunflower oil, with or without additives, was added to the wells in each row. The plate was shaken gently for eighteen hours, and optical density measurements were taken with a plate-reader at 550 nm. A low absorbance value indicates a low level of scattering of light, and corresponds to effective dispersion of protein in oil.

Employing the method described above, the effect of addition of acetic acid, sorbic acid and oleic acid to sunflower oil (at a concentration of 1% wt:vol) in facilitating dispersion of aprotinin, using soya phosphatidyl choline as amphiphile, is demonstrated. The results, expressed in terms of optical density as a function of phosphatidyl choline concentration (at constant protein concentration) are given in the table and FIG. 4.

| mg PC per well | Oil alone | +Oleic acid | +Acetic acid | +Sorbic acid |
|---|---|---|---|---|
| 2.5 | 0.124 | 0.052 | 0.021 | 0.025 |
| 5 | 0.087 | 0.036 | −0.002 | −0.009 |
| 7.5 | 0.1 | 0.073 | 0.04 | 0.005 |
| 10 | 0.259 | 0.236 | 0.004 | 0.008 |

EXAMPLE 4

Aprotinin was dissolved in distilled water at a concentration of 20 mg/ml and dispensed into wells of a microplate, each well in a row of five receiving 0, 12.5, 16.6, 25, and 50 $\mu$l respectively. In addition, soya phosphatidyl choline, dispersed in distilled water by probe sonication for ten minutes with cooling, was added to each well at a concentration of 100 mg/ml, wells in each row receiving 100 $\mu$l. The contents of the wells were mixed by gentle shaking, then frozen at −20° C., then lyophilised overnight.

The following day, 100 $\mu$l of sunflower oil, with or without additives, was added to the wells in each row. The plate was shaken gently for eighteen hours, and optical density measurements were taken with a plate-reader at 550 nm. A low absorbance value indicates a low level of scattering of light, and corresponds to effective dispersion of protein in oil.

Employing the method described above, the effect of addition of phenol, benzoic acid, caproic acid, valearic acid, acetic acid and sorbic acid to sunflower oil (at a concentration of 1% wt:vol) in facilitating dispersion of aprotinin, using soya phosphatidyl choline as amphiphile, is demonstrated. The results, expressed in terms of optical density as a function of protein oncentration (at constant phosphatidyl choline concentration) are given in the table and FIG. 5.

| Aprot (mg/well) | 0 | 0.25 | 0.33 | 0.5 | 1 |
|---|---|---|---|---|---|
| Phenol | 0.017 | 0.041 | 0.046 | 0.053 | 0.163 |
| Benzoic acid | 0.024 | 0.019 | 0.023 | 0.035 | 0.145 |
| Caproic acid | 0.018 | 0.031 | 0.029 | 0.041 | 0.151 |
| Valearic acid | 0.02 | 0.016 | 0.019 | 0.039 | 0.132 |
| Acetic acid | 0.031 | 0.023 | 0.016 | 0.04 | 0.105 |
| Sorbic acid | 0.012 | 0.032 | 0.038 | 0.039 | 0.19 |
| Oil alone | 0.155 | 0.1845 | 0.169 | 0.1915 | 0.322 |

EXAMPLE 5

Aprotinin was dissolved in distilled water at a concentration of 20 mg/ml and dispensed into wells of a microplate, each well in a row of six receiving 0, 12.5, 16.6, 25, 33 and 50 $\mu$l respectively. In addition, soya phosphatidyl choline, dispersed in distilled water by probe sonication for ten minutes with cooling, was added to each well at a concentration of 100 mg/ml, wells in each row receiving 100 $\mu$l. The contents of the wells were mixed by gentle shaking, then frozen at −20° C., then lyophilised overnight.

The following day, 100 $\mu$l of sunflower oil, with or without additives, was added to the wells in each row. The plate was shaken gently for eighteen hours, and optical density measurements were taken with a plate-reader at 550 nm. A low absorbance value indicates a low level of scattering of light, and corresponds to effective dispersion of protein in oil.

Employing the method described above, the effect of addition of valearic acid and triethylamine to sunflower oil (at a concentration of 1% wt:vol) in facilitating dispersion of aprotinin, using soya phosphatidyl choline as amphiphile, is demonstrated. The results, expressed in terms of optical density as a function of protein concentration (at constant phosphatidyl choline concentration) are given in the table and FIG. 6.

| Aprot (mg/well) | 0 | 0.33 | 0.5 | 0.66 | 1 |
|---|---|---|---|---|---|
| Oil alone | 0.166 | 0.176 | 0.193 | 0.261 | 0.28 |
| Valeric acid | 0.017 | 0.038 | 0.053 | 0.071 | 0.144 |
| Valeric acid + TEA | 0.021 | 0.023 | 0.045 | 0.062 | 0.134 |
| TEA | 0.254 | 0.152 | 0.206 | 0.24 | 0.381 |

EXAMPLE 6

Aprotinin was dissolved in distilled water at a concentration of 20 mg/ml and dispensed into wells of a microplate, each well in a row of six receiving 0, 12.5, 16.6, 25, 33 and 50 $\mu$l respectively. In addition, soya phosphatidyl choline, dispersed in distilled water by probe sonication for ten minutes with cooling, was added to each well at a concentration of 100 mg/ml, wells in each row receiving 100 $\mu$l. The contents of the wells were mixed by gentle shaking, then frozen at −20° C., then lyophilised overnight.

The following day, 100 $\mu$l of sunflower oil, with or without additives, was added to the wells in each row. The plate was shaken gently for eighteen hours, and optical density measurements were taken with a plate-reader at 550 nm. A low absorbance value indicates a low level of scattering of light, and corresponds to effective dispersion of protein in oil.

Employing the method described above, the effect of addition of benzyl boronic acid, benzoic acid and salicylic acid to sunflower oil (at a concentration of 1% wt:vol) in facilitating dispersion of aprotinin, using soya phosphatidyl choline as amphiphile, is demonstrated. The results, expressed in terms of optical density as a function of protein concentration (at constant phosphatidyl choline concentration) are given in the table and FIG. 7.

| Aprot (mg/well) | 0 | 0.25 | 0.33 | 0.5 | 0.66 | 1 |
|---|---|---|---|---|---|---|
| Benzyl boric acid | 0.007 | 0.015 | 0.024 | 0.046 | 0.087 | 0.188 |
| Benzoic acid | 0.002 | 0.008 | 0.014 | 0.045 | 0.08 | 0.169 |
| Salicylic acid | 0.005 | 0.003 | 0.003 | 0.005 | 0.015 | 0.06 |
| Oil alone | 0.04 | 0.137 | 0.172 | 0.236 | 0.275 | 0.285 |

EXAMPLE 7

Aprotinin was dissolved in distilled water at a concentration of 20 mg/ml and dispensed into wells of a microplate, each well in a row of five receiving 0, 12.5, 25, 37.5 and 50 $\mu$l respectively. In addition, soya phosphatidyl choline, dispersed in distilled water by probe sonication for ten minutes with cooling, was added to each well at a concentration of 100 mg/ml, wells in each row receiving 100 $\mu$l. The contents of the wells were mixed by gentle shaking, then frozen at −20° C., then lyophilised overnight.

The following day, 100 $\mu$l of sunflower oil, with or without additives, was added to the wells in each row. The plate was shaken gently for eighteen hours, and optical density measurements were taken with a plate-reader at 550 nm. A low absorbance value indicates a low level of scattering of light, and corresponds to effective dispersion of protein in oil.

Employing the method described above, the effect of addition of benzoic acid, salicylic acid, p-cresol, benzoyl alcohol, nitrobenzene and acetic acid to sunflower oil (at a concentration of 1% wt:vol) in facilitating dispersion of aprotinin, using soya phosphatidyl choline as amphiphile, is demonstrated. The results, expressed in terms of optical density as a function of protein concentration (at constant phosphatidyl choline concentration) are given in the table and FIG. 8.

| Nature of | Aprot (mg/well) | | | | |
|---|---|---|---|---|---|
| facilitator | 0 | 0.25 | 0.5 | 0.75 | 1 |
| None | 0.044 | 0.101 | 0.111 | 0.165 | 0.244 |
| Benzoic Acid | 0.006 | 0.01 | 0.025 | 0.052 | 0.112 |
| Salicylic Acid | −0.004 | 0.005 | 0.007 | 0.028 | 0.095 |
| p Cresol | −0.004 | 0.02 | 0.061 | 0.121 | 0.192 |
| Benzyl alcohol | 0.017 | 0.03 | 0.051 | 0.165 | 0.229 |
| Nitro benzene | 0.006 | 0.018 | 0.12 | 0.209 | 0.206 |
| Acetic Acid | 0.037 | 0.036 | 0.0556 | 0.095 | 1.161 |

EXAMPLE 8

Wells of a microplate were filled with aprotinin and soya phosphatidyl choline as described in example 7, and lyophilised overnight.

The following day, 100 μl of jojoba oil, with or without additives, was added to the wells in each row. The plate was shaken gently for eighteen hours, and optical density measurements were taken with a plate-reader at 550 nm. A low absorbance value indicates a low level of scattering of light, and corresponds to effective dispersion of protein in oil.

Employing the method described above, the effect of addition of salicylic acid to jojoba oil (at a concentration of 1% wt:vol) in facilitating dispersion of aprotinin, using soya phosphatidyl choline as amphiphile, is demonstrated. The results, expressed in terms of optical density as a function of protein concentration (at constant phosphatidyl choline concentration) are given in the table and FIG. 9.

| Aprot (mg/well) | 0 | 0.25 | 0.5 | 0.75 | 1 |
|---|---|---|---|---|---|
| Jojoba oil | 0.249 | 0.539 | 0.798 | 0.744 | 0.629 |
| Jojoba oil + sal | 0.017 | 0.021 | 0.047 | 0.09 | 0.216 |

EXAMPLE 9

Wells of a microplate were filled with aprotinin and soya phosphatidyl choline as described in example 7, and lyophilised overnight.

The following day, 100 μl of squalane, with or without additives, was added to the wells in each row. The plate was shaken gently for eighteen hours, and optical density measurements were taken with a plate-reader at 550 nm. A low absorbance value indicates a low level of scattering of light, and corresponds to effective dispersion of protein in oil.

Employing the method described above, the effect of addition of caproic acid, benzoic acid and phenol to squalane (at a concentration of 1% wt:vol) in facilitating dispersion of aprotinin, using soya phosphatidyl choline as amphiphile, is demonstrated. The results, expressed in terms of optical density as a function of protein concentration (at constant phosphatidyl choline concentration) are given in the table and FIG. 10.

| Nature of | Aprot (mg/well) | | | | |
|---|---|---|---|---|---|
| facilitator | 0 | 0.25 | 0.5 | 0.75 | 1 |
| None | 0.735 | 0.495 | 1.004 | 1.014 | 1.32 |
| caproic acid | 0.059 | 0.024 | 0.022 | 0.03 | 0.11 |
| phenol | 0.061 | 0.099 | 0.052 | 0.192 | 0.094 |
| benzoic acid | 0.198 | 0.054 | 0.069 | 0.034 | 0.085 |
| ethanol | 0.5 | 0.651 | 0.912 | 0.826 | 0.811 |

EXAMPLE 10

Wells of a microplate were filled with aprotinin and lyso-phosphatidyl choline as described in example 7, and lyophilised overnight.

The following day, 100 μl of phytol or octanol, with or without additives, was added to the wells in each row. The plate was shaken gently for eighteen hours, and optical density measurements were taken with a plate-reader at 550 nm. A low absorbance value indicates a low level of scattering of light, and corresponds to effective dispersion of protein in oil.

Employing the method described above, the effect of addition of salicylic acid to phytol or octanol (at a concentration of 1% wt:vol) in facilitating dispersion of aprotinin, using lyso-phosphatidyl choline as amphiphile, is demonstrated. The results, expressed in terms of optical density as a function of protein concentration (at constant lyso-phosphatidyl choline concentration) are given in the table and FIG. 11.

| Aprot (mg/well) | 0 | 0.25 | 0.5 | 0.75 | 1 |
|---|---|---|---|---|---|
| Phytol | 0.023 | 0.147 | 0.533 | 0.636 | 0.667 |
| Phytol + sal | 0.011 | 0.009 | 0.005 | 0.003 | 0.179 |
| Octanol | 0.013 | 0.044 | 0.021 | 0.302 | 0.741 |
| Octanol + sal | 0.042 | 0.014 | 0.014 | 0.009 | 0.024 |

EXAMPLE 11

Aprotinin was dissolved in distilled water at a concentration of 20 mg/ml and dispensed into wells of a microplate, each well in a row of six receiving 0, 12.5, 16.6, 26, 33 and 50 μl respectively. Soya phosphatidyl choline was dispersed in distilled water by probe sonication for ten minutes with cooling, and sorbic acid was incorporated by mixing solid sorbic acid with one ml aliquots of the dispersed phospholipid to give concentrations of 1, 0.5, 0.25, 0.125 and 0.0625% in aqueous phase. 100 μl of each phospholipid suspension was added to a fresh row of six wells each. The contents of the wells were mixed by gentle shaking, frozen at −20° C., then lyophilised overnight.

The following day, 100 μl of sunflower oil, with or without additives, was added to the wells in each row. The plate was shaken gently for eighteen hours, and optical density measurements were taken with a plate-reader at 550 nm. A low absorbance value indicates a low level of scattering of light, and corresponds to effective dispersion of protein in oil.

Employing the method described above, the effect of addition of sorbic acid to the phosphatidyl choline dispersion at different concentrations in facilitating dispersion of aprotinin in sunflower oil is demonstrated. The results, expressed in terms of optical density as a function of protein and sorbic acid concentration (at constant phosphatidyl choline concentration) are given in the table and FIG. 12.

| Aprot\sorbic acid | 0 | 0.0625 | 0.125 | 0.25 | 0.5 | 1 |
|---|---|---|---|---|---|---|
| 0.25 | 0.049 | 0.062 | 0.073 | 0.02 | 0.012 | 0.008 |
| 0.5 | 0.147 | 0.113 | 0.14 | 0.085 | 0.042 | 0.004 |
| 0.66 | 0.23 | 0.162 | 0.18 | 0.124 | 0.074 | 0.071 |
| 1 | 0.366 | 0.271 | 0.251 | 0.198 | 0.127 | 0.143 |

EXAMPLE 12

Phospholipid dispersions were prepared as described in example 7 containing either 100 mg of soya phosphatidyl choline per ml of distilled water, or 90 mg of phosphatidyl choline and 10 mg of phosphatidic acid per ml of distilled water. Wells of a microplate were filled with aprotinin and one or other of the phospholipid dispersions above as described in example 7, and lyophilised overnight.

The following day, 100 μl of Miglyol 818 or oleic acid was added to the wells in each row. The plate was shaken gently for eighteen hours, and optical density measurements were taken with a plate-reader at 550 nm. A low absorbance value indicates a low level of scattering of light, and corresponds to effective dispersion of protein in oil.

Employing the method described above, the effect of inclusion of phosphatidic acid in the phospholipid suspension in facilitating dispersion of aprotinin in Miglyol 818 or oleic acid is demonstrated. The results, expressed in terms of optical density as a function of protein concentration (at constant phospholipid concentration) are given in the table and accompanying FIGS. 13 and 14.

| Aprot (mg/well) | 0 | 0.25 | 0.5 | 0.75 | 1 |
|---|---|---|---|---|---|
| M818 | | | | | |
| PC | 0.014 | 0.014 | 0.036 | 0.073 | 0.238 |
| PC/PA | 0.028 | 0.037 | 0.041 | 0.045 | 0.059 |
| Oleic acid | | | | | |
| PC | 0.013 | 0.023 | 0.11 | 0.223 | 0.304 |
| PC/PA | 0.04 | 0.04 | 0.045 | 0.048 | 0.087 |

EXAMPLE 13

Phospholipid dispersions were prepared as described in example 7 containing either 100 mg of soya phosphatidyl choline per ml of distilled water, or 90 mg of phosphatidyl choline and 10 mg of phosphatidic acid per ml of distilled water. Wells of a microplate were filled with aprotinin and one or other of the phospholipid dispersions above as described in example 7, and lyophilised overnight.

The following day, 100 μl of cod liver oil was added to the wells in each row. The plate was shaken gently for eight hours, and optical density measurements were taken with a plate-reader at 550 nm. A low absorbance value indicates a low level of scattering of light, and corresponds to effective dispersion of protein in oil.

Employing the method described above, the effect of inclusion of phosphatidic acid in the phospholipid suspension in facilitating dispersion of aprotinin in cod liver oil is demonstrated. The results, expressed in terms of optical density as a function of protein concentration (at constant phospholipid concentration) are given in the table and FIG. 15.

| | Apoprotein Concentration | | | | |
|---|---|---|---|---|---|
| Nature of oil +/− PA | 0 | 0.25 | 0.5 | 0.75 | 1 |
| PC/Cod liver | 0.341 | 0.578 | 0.936 | 1.169 | 1.124 |
| PC:PA/Cod liver | 0.119 | 0.339 | 0.198 | 0.174 | 0.756 |

EXAMPLE 14

Phospholipid dispersions were prepared as described in example 7 containing either 100 mg of soya phosphatidyl choline per ml of distilled water, or 90 mg of phosphatidyl choline and 10 mg of either phosphatidic acid or cholesterol hemisuccinate per ml of distilled water. Wells of a microplate were filled with aprotinin and one or other of the phospholipid dispersions above as described in example 7, and lyophilised overnight.

The following day, 100 μl of squalane or sunflower oil was added to the wells in each row. The plate was shaken gently for eight hours, and optical density measurements were taken with a plate-reader at 550 nm. A low absorbance value indicates a low level of scattering of light, and corresponds to effective dispersion of protein in oil.

Employing the method described above, the effect of inclusion of phosphatidic acid or cholesterol hemisuccinate in the phospholipid suspension in facilitating dispersion of aprotinin in squalane or sunflower oil is demonstrated. The results, expressed in terms of optical density as a function of protein concentration (at constant phospholipid concentration) are given in the table and FIGS. 16 and 17.

| | Apoprotein Concentration | | | | |
|---|---|---|---|---|---|
| Nature of facilitator | 0 | 0.25 | 0.5 | 0.75 | 1 |
| Squalane | | | | | |
| PC alone | 0.773 | 0.685 | 0.475 | 0.544 | 0.601 |
| PC + Chems | 0.086 | 0.093 | 0.085 | 0.071 | 0.095 |
| PC + PA | 0.074 | 0.033 | 0.032 | 0.032 | 0.051 |
| Sunflower oil | | | | | |
| PC alone | 0.342 | 0.308 | 0.203 | 0.484 | 0.593 |
| PC + Chems | 0.241 | 0.261 | 0.172 | 0.3 | 0.412 |
| PC + PA | 0.168 | 0.336 | 0.079 | 0.06S | 0.088 |

EXAMPLE 15

Phospholipid dispersions were prepared as described in example 7 containing either 100 mg of soya phosphatidyl choline per ml of distilled water, or 90 mg of phosphatidyl choline and 10 mg of phosphatidic acid per ml of distilled water. Wells of a microplate were filled with aprotinin and one or other of the phospholipid dispersions above as described in example 7, and lyophilised overnight.

The following day, 100 μl of jojoba oil was added to the wells in each row. The plate was shaken gently for fifty three hours, and optical density measurements were taken with a plate-reader at 550 nm. A low absorbance value indicates a low level of scattering of light, and corresponds to effective dispersion of protein in oil.

Employing the method described above, the effect of inclusion of phosphatidic acid in the phospholipid suspension in facilitating dispersion of aprotinin in jojoba oil is demonstrated. The results, expressed in terms of optical density as a function of protein concentration (at constant phospholipid concentration) are given in the table and FIG. 18.

| Jojoba Oil | | | | | |
|---|---|---|---|---|---|
| | Apoprotein Concentration | | | | |
| Nature of facilitator | 0 | 0.25 | 0.5 | 0.75 | 1 |
| PC alone | 0.439 | 0.435 | 0.623 | 0.546 | 0.112 |
| PC + PA | 0.154 | 0.16 | 0.08 | 0.073 | 0.087 |

EXAMPLE 16

Phospholipid dispersions were prepared as described in example 7 containing either 100 mg of soya phosphatidyl choline per ml of distilled water, or 90 mg of phosphatidyl choline and 10 mg of α-tocopherol succinate per ml of distilled water. Wells of a microplate were filled with 25 μl of aprotinin solution and one or other of the phospholipid dispersions above as described in example 7, and lyophilised overnight.

The following day, 100 μl of Miglyol 818 was added to the wells in each row. The plate was shaken gently for eighteen hours, and optical density measurements were taken with a plate-reader at 550 nm. A low absorbance value indicates a low level of scattering of light, and corresponds to effective dispersion of protein in oil.

Employing the method described above, the effect of inclusion of α-tocopherol succinate in the phospholipid suspension in facilitating dispersion of aprotinin in Miglyol 818 is demonstrated. The results, expressed in terms of optical density as a function of protein concentration (at constant phospholipid concentration) are given in the table and FIG. 19.

| Aprot (mg/well) | 0 | 0.5 |
|---|---|---|
| PC alone | 0.051 | 0.085 |
| PC + tocopherol succinate | 0.036 | 0.037 |

EXAMPLE 17

Aprotinin was dissolved in distilled water at a concentration of 20 mg/ml and dispensed into one set of five B2 glass vials (Group I) receiving 0, 125, 250, 375 and 500 μl respectively. In addition, 1 ml of soya phosphatidyl choline, dispersed in distilled water by probe sonication for ten minutes with cooling, was added to each vial at a concentration of 100 mg/ml. A second set of vials (Group II) received 0, 62.5, 125, 187.5 and 250 μl of aprotinin solution as described above, together with 0.5 ml of soya phospholipid dispersion (100 mg/ml).The contents of the vials were mixed by gentle shaking, then frozen in liquid nitrogen, and lyophilised overnight.

The following day, 1 ml of Miglyol 818 was added to each vial in Group I, and 0.5 ml of Miglyol 818 containing 10 mg salicylic acid per ml was added to all vials in Group II. All vials flushed with nitrogen, sealed and mixed at room temperature on a roller mixer until the oil dispersions in Group II (with salicylic acid as facilitator) were all essentially clear (three hours). 400 μl of each of the oils from Group I were then transferred to fresh vials each containing 4 mg of dry solid salicylic acid, and the vials were sealed, flushed with nitrogen, and roller mixing continued. The tubes were incubated in this way for up to five days, and optical density measurements at 550 nm were taken on 100 μl samples removed from the tubes at intervals, and dispensed into a plate-reader. A low absorbance value indicates a low level of scattering of light, and corresponds to effective dispersion of protein in oil.

Employing the method described above, the effect of addition of salicylic acid (at a concentration of 1% wt:vol) either before or after mixing of oil with the protein/lipid complex in facilitating dispersion of aprotinin, using soya phosphatidyl choline as amphiphile, is demonstrated. The results, expressed in terms of optical density as a function of protein concentration (at constant phosphatidyl choline concentration) are given in the table and FIG. 20.

| Optical Density at 550 nm after incubation at room temperature for five days | | | |
|---|---|---|---|
| Aprotinin | no facilitator | facilitator in oil before addition | facilitator added after oil |
| 0 | 0 | 0 | 0 |
| 0.25 | 0.002 | 0 | 0 |
| 0.5 | 0.443 | 0.004 | 0.017 |
| 0.75 | 0.488 | 0.009 | 0.016 |
| 1 | 0.866 | 0.002 | 0.128 |

EXAMPLE 18

An aqueous dispersion of soy phosphatidyl choline (soy PC) was prepared, containing 100 mg/g of suspension, flushed thoroughly with nitrogen, and sonicated at an amplitude of 8 microns peak to peak. Each aliquot was subjected to a total sonication time of 4 minutes, in pulses of 30 seconds interspersed by cooling for 30 seconds in an ice slurry bath. The resulting opalescent dispersion of small unilamellar vesicles (SUV) was then centrifuged for 15 minutes to remove particles of titanium.

5 mg of lipase from Candida cylindericae was dissolved in distilled water to a concentration of 100 mg/g, and 50 microL aliquots (i.e. 0.5 mg lipase each) were added to small glass test tubes. To each tube was added 100 μl of SUV (ie 10 mg of PC) , and the contents mixed, shell-frozen in liquid nitrogen and freeze-dried overnight. 665 mg of linoleic acid was added to each lyophilate, mixed by vortexing and then left for 1 hour to disperse. To the resulting clear suspensions were added 335 mg of trilinolein followed by mixing. It was noted that addition of the triglyceride had no adverse effect on the clarity of the dispersions, whereas direct addition of trilinolein to such lyophilates would normally not allow such dispersion to take place. After incubating for 1 week at 37° C. there was no change in the clarity of the dispersions. Thus, solubilization of the protein in the presence of a long chain triglyceride, has been enabled by the presence of linoleic acid.

EXAMPLE 19

A solution of lipase from Mucor mehii, containing 8.9 mg protein/ml was distributed into aliquots of 0.1 ml (0.89 mg protein) in small glass vials. To each was added 200 mg of SUV containing 100 mg PC/g (i.e. 20 mg PC per vial) prepared as in example 1, and the mixtures were lyophilised overnight. 50% of the lyophilates were dispersed with 665 mg of oleic acid and the remainder with the same amount of linoleic acid. The dispersions were left for 3 hours by which time they were completely clear, and then 335 mg trilinolein was added to the oleic acid dispersions and the same amount of triolein to the linoleic acid-based ones. Both types remained clear and were still so after 2 weeks of incubation at 37° C.

EXAMPLE 20

Lyophilates prepared as above, each containing 1 mg of aprotinin (from 100 microl of a 1% solution) and 20 or 30 mg soy PC (from 200 or 300 μl of SUV respectively), were dispersed with sunflower oil containing 0, 10, 20 and 30% oleic acid (w/w). All of those containing oleic acid became clear or slightly opalescent, while the oleic acid-free preparation remained as a turbid suspension. Similarly, a lyophilate mixed with the more saturated corn oil, containing 10% (w/w) oleic acid, formed a slightly opalescent dispersion while a control mixed with pure corn oil formed a turbid suspension.

EXAMPLE 21

Five columns of 4 rows of small test-tubes were set up. To all the tubes in each row, in the 1st, 2nd, 3rd and 4th rows, were added aliquots containing 0.36, 0.72, 1.08 and 1.44 mg aprotinin respectively (aprotinin was added as an aqueous solution containing 10 mg protein/ml). To every tube was then added 180 μl of SUV containing 100 mg PC/ml (ie 18 mg PC added), prepared as in Example 1 The tube contents were mixed, shell-frozen and freeze-dried overnight. To all of the tubes in each of columns 1, 2, 3, 4 and 5, was then added 180 mg of sunflower oil containing 5, 3, 2, 1 and 0% oleic acid respectively. The tubes were mixed by vortexing and left to disperse overnight, after which the dispersions were transferred to a microtitre plate and absorbances read at 550 nm. The results are shown in Table 1.

TABLE 1

Effect of oleic acid on solubilisation of aprotinin in sunflower oil

| Aprotinin content | Oleic acid content of sunf lower oil (%) | | | | |
|---|---|---|---|---|---|
| (mg) | 5 | 3 | 2 | 1 | 0 |
| 0.36 | 0.029 | 0.018 | 0.023 | 0.022 | 0.469 |
| 0.72 | 0.052 | 0.054 | 0.048 | 0.06 | 0.128 |
| 1.06 | 0.017 | 0.017 | 0.099 | 0.176 | 0.208 |
| 1.44 | 0.182 | 0.182 | 0.162 | 0.104 | 0.286 |

EXAMPLE 22

Two rows of small test-tubes were set up. Into each tube of the first row was added 0.2 ml of 0.25% ascorbic acid solution (i.e. 0.5 mg ascorbic acid), and into the second, 0.2 ml of 0.125% solution (0.25 mg ascorbic acid). 60 μl of soy PC SUV prepared as in Example 1, was added to each tube, and the contents shell-frozen and freeze-dried overnight. To the lyophilates in the 1st, 2nd, 3rd and 4th tube in each row was added 300 mg of sunflower oil solutions containing 1, 2, 3 and 4% of linoleic acid respectively. The tubes were vortexed briefly and then left to disperse. After 24 hours the dispersions were examined visually and the degrees of clarity listed on a score of 1 to 10. A score of 10 means completely clear while 1 means that apparently, no solubilization had taken place. The results are shown in Table 2.

TABLE 2

Effect of linoleic acid on solubilisation of ascorbic acid in sunflower oil

| Ascorbic acid | Linoleic acid content of sunflower oil (%) | | | |
|---|---|---|---|---|
| content (mg) | 1 | 2 | 3 | 4 |
| 0.25 | 9+ | 10 | 10 | 10 |
| 0.5 | 7 | 8 | 10 | 10 |

EXAMPLE 23

A stock solution of 400 mM glycerol was prepared and diluted sequentially to give 200, 100, 50 and 25 mM solutions. Into each of 6 small test-tubes was added 200 μl of a solution containing 18 mg of aprotinin/ml, and then across the row from left to right was added 75 μl of distilled water, 25, 50, 100, and 200 mM glycerol respectively. To each tube was then added 300 μl of soy PC SUV prepared as in Example 1, and the mixtures were shell-frozen, freeze-dried overnight and the lyophilates dispersed each with 300 mg of Miglyol 818. After vortexing and standing overnight, the dispersions were transferred to a microtitre plate and the absorbances measured at 550 nm. The results are shown in Table 3.

TABLE 3

Effect of glycerol on solubilisation of Aprotinin in Miglyol 818

| | Concentration of added glycerol (mM) | | | | | |
|---|---|---|---|---|---|---|
| | 0 | 25 | 50 | 100 | 200 | 400 |
| Absorption (550 nm) | 0.152 | 0.073 | 0.052 | 0.037 | 0.05 | 0.361 |

EXAMPLE 24 i) 100 mg of ovalbumin was dissolved in 5 ml of distilled water.

ii) 20 mg of proline, serine, glutamic acid and tyrosine were each dissolved in 1ml of distilled water.

iii) Phospholipid was dispersed in distilled water at a concentration of 250 mg/ml according to the method described in previous examples.

iv) The solutions prepared in the steps above were dispersed into two ml glass vials as follows:

| Label | 0 | 1 | 2 | 3 | mg/vial |
|---|---|---|---|---|---|
| PC (l) | 90 | 90 | 90 | 90 | 22.5 |
| Ovalbumin (l) | 100 | 100 | 100 | 100 | 2 |
| Amino acid (l) | 0 | 12.5 | 25 | 50 | 0–1 |
| Amino acid (mg) | 0 | 0.25 | 0.5 | 1.0 | 0–1 |

v) The contents of all the tubes were mixed well, frozen in liquid nitrogen and hyophilised overnight.

vi) The following day, 0.2 ml of Miglyol M840 was added to the contents of each vial and shaken at RT.

vii) The following day, 501 samples were transferred to the wells of a microplate, and the optical densities measured at 600 nm wavelength.

The measurements obtained are shown in the table below:

| | 0 | 1 | 2 | 3 |
|---|---|---|---|---|
| Glutamic acid | 0.31 | 0.197 | 0.194 | 0.224 |
| Proline | 0.27 | 0.196 | 0.163 | 0.15 |
| Serine | 0.287 | 0.171 | 0.147 | 0.131 |
| Tyrosine | 0.324 | 0.253 | 0.213 | 0.21 |

These results are shown in FIG. 21.

It can be seen that addition of the amino acids to the aqueous phase during incorporation of the protein into oil significantly reduced the turbidity of the final formulation, indicating an improvement in solubilisation due to the amino acids.

We claim:

1. A process for the preparation of an essentially anhydrous single phase hydrophobic preparation comprising a hydrophilic species in a hydrophobic solvent, the process comprising (i) performing step (a), (b) or (c) as follows:

(a) mixing a hydrophilic species with a phosphoryl choline-containing amphiphile in a hydrophilic solvent, wherein the amphiphile forms micelles in the hydrophilic solvent and wherein the mixing gives a micellar solution;

(b) mixing a phosphoryl choline-containing amphiphile with a hydrophilic solvent, wherein the amphiphile forms vesicles in the hydrophilic solvent, to give a mixture, treating the mixture in such a way as to form a dispersion of small unilamellar vesicles and adding a hydrophilic species; or (c) co-solubilizing a hydrophilic species and a phosphoryl choline-containing amphiphile in a common solvent;

(ii) removing the solvent or solvents to leave an array of the amphiphile molecules with their hydrophilic head groups orientated towards the hydrophilic species and wherein there is no chemical interaction between the amphiphile and the hydrophilic species; and (iii) adding a hydrophobic solvent to the hydrophilic species/amphiphile array to give a hydrophobic composition comprising the hydrophilic species.

(iv) adding a compound selected from the group consisting of:

(a) carboxylic acids, amino acids, benzyl alcohol, ethanol, t-butanol, i-propanol and glycerol monooleate;

(b) lipid-soluble organic acids;

(c) acidic amphiphiles;

(d) glycerol and other polyhydric alcohols; and (e) mixtures of the above;

at a stage of the process selected from the group consisting of stages (i), (ii) and (iii).

2. The process as claimed in claim 1 wherein the hydrophilic species is selected from the group consisting of macromolecules, small organic molecules, small inorganic molecules and colloidal substances.

3. The process as claimed in claim 2 wherein the macromolecule is selected from the group consisting of proteins, glycoproteins, oligo-nucleic acids, polynucleic acids, polysaccharides and supramolecular assemblies thereof.

4. The process as claimed in claim 3 wherein the protein is selected from the group consisting of insulin, calcitonin, haemoglobin, cytochrome C, horseradish peroxidase, aprotinin, mushroom tyrosinase, erythropoietin, somatotropin, growth hormone, growth hormone releasing factor, galanin, urokinase, Factor IX, tissue plasminogen activator, superoxide dismutase, catalase, peroxidase, ferritin, interferon, Factor VIII and fragments thereof.

5. The process as claimed in claim 2 wherein the small organic or inorganic molecule is selected from the group consisting of glucose, calcium chloride and sodium phosphate.

6. The process as claimed in claim 1, which was step (i)(b) wherein the amphile is phosphatidyl choline or sphingomyelin.

7. The process as claimed in claim 1, which uses step (i)(a) wherein the amphiphile is selected from the group consisting of lyso-phosphatidyl choline, hexadecyl phosphocholine, amphiphile polymers containing phosphoryl choline and derivatives thereof.

8. The process as claimed in claim 1, wherein the hydrophobic solvent is selected from the group consisting of mineral oil, squalene, squalane, medium chain alcohols, branched long chain alcohols, monoglycerides, diglycerides, medium chain triglycerides and long chain triglycerides.

9. The process as claimed in claim 1, wherein the amphiphile comprises pliosphatidyl choline and the hydrophobic solvent is a triglyceride.

10. The process as claimed in claim 1, wherein in step (i), the hydrophilic solvent is water.

11. The process as claimed in claim 1 which includes step (i)(a) or step (i)(b) and wherein in step (ii), the hydrophilic solvent is removed by lyophilization.

12. The process as claimed in claim 1, which uses step (i)(c) and wherein the weight ratio of the phosphoryl choline-containing amphiphile to the hydrophilic species is from about 1:1 to about 50:1.

13. The process as claimed in claim 1 wherein the lipid soluble organic acid is selected from the group consisting of carboxylic acids, phenol, p-cresol, phenyl-boronic acid, benzyl boric acid, phenyl-sulfonic acid, phenyl-arsenic acid, benzoic acid, salicylic acid, acetic acid, sorbic acid, valearic acid, oleic acid and caproic acid.

14. The process as claimed in claim 11 wherein the acidic amphiphile is selected from the group consisting of cholesterol hemisuccinate, α-tocopherol, α-tocopherol succinate, phosphatidic acid, phosphatidyl-glycerol, phosphatidylinositol and lyso derivatives of any of the phosphatides.

* * * * *